(12) United States Patent
Tomiyama et al.

(10) Patent No.: US 6,414,001 B2
(45) Date of Patent: Jul. 2, 2002

(54) ETHER AND AMIDE COMPOUNDS PREPARATION THEREOF COMPOSITION CONTAINING SAME AND USE THEREOF AS ANTIDIADETICS

(75) Inventors: Tsuyoshi Tomiyama; Akira Tomiyama; Hiroshi Tomiyama, all of Hanishina-gun; Keiko Kuroiwa, Ueda, all of (JP)

(73) Assignee: Kotobuki Pharmaceutical Co. Ltd., Nagano (JP)

(*) Notice: Subject to any disclaimer, the term of this patent is extended or adjusted under 35 U.S.C. 154(b) by 0 days.

(21) Appl. No.: 09/756,701

(22) Filed: Jan. 10, 2001

(30) Foreign Application Priority Data

Jan. 11, 2000 (JP) .................................. 2000-006106
Nov. 22, 2000 (JP) .................................. 2000-356303

(51) Int. Cl.[7] ......................... A61K 31/42; C07D 263/30
(52) U.S. Cl. ......................... 514/374; 548/235
(58) Field of Search ......................... 548/235; 514/374

(56) References Cited

U.S. PATENT DOCUMENTS 6,204,277 B1 * 3/2001 Shinkai et al. ............... 514/374

FOREIGN PATENT DOCUMENTS

| WO | 9613264 | 5/1996 |
| WO | 0116111 | 3/2001 |
| WO | 0116119 | 3/2001 |

\* cited by examiner

*Primary Examiner*—Alan L. Rotman
*Assistant Examiner*—Rita Desai
(74) *Attorney, Agent, or Firm*—Sherman & Shalloway

(57) ABSTRACT

Ether and amide derivatives are disclosed, which are represented by the following formula (I) and its pharmaceutical acceptable salt, and which are useful for the treatment of diabetes.

$$R_1—A—R_2 \quad (I)$$

wherein

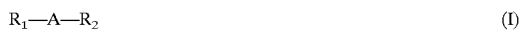

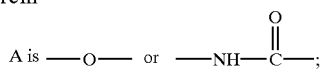

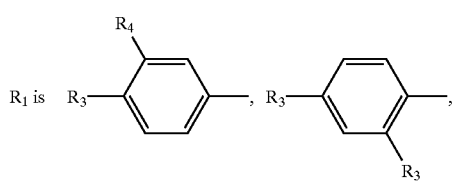

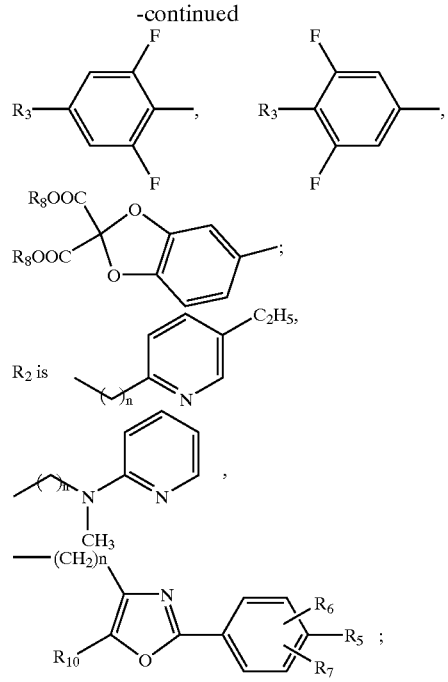

(with the provisos that (i) when A is —O—, then n is 2 or 3 (ii) when

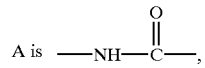

then n is 1 or 2. $R_3$ is OH—, $CH_3SO_2NH$—, $CF_3SO_2NH$—, $CH_3SO_2NHCH_2$—, $CF_3SO_2NHCH_2$—, HOOC—, $CH_3OOC$—,

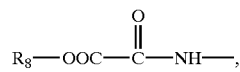

HOOC—$CH_2SO_2NH$—, $CF_3$—$CH_2SO_2NH$—,

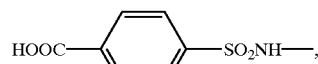

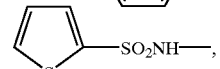

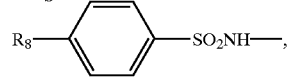

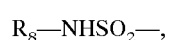

$R_8$—$NHSO_2$—$CH_2$—, HOOC—$CH_2$—O—, $HSO_3N$=CH—, or $R_9$—$SO_2NHCO$—;
$R_4$ is H, OH, O-alkyl or O—$CH_2OCH_3$;
$R_5$ is H, halogen atom, —$CH_2COOH$ or OH;
$R_6$ and $R_7$ are hydrogen, t-butyl or pyrolidyl;
$R_8$ is hydrogen or lower alkyl;
$R_9$ is alkyl or thienyl;
$R_{10}$ is lower alkyl)
or a pharmaceutically acceptable salt.

5 Claims, No Drawings

ETHER AND AMIDE COMPOUNDS PREPARATION THEREOF COMPOSITION CONTAINING SAME AND USE THEREOF AS ANTIDIADETICS

BACKGROUND OF THE INVENTION

1. Field of the Invention

This invention relates to new ether and/or amide derivatives, which are useful for the treatment of diabetes and a pharmaceutical containing these compounds as active ingredients.

2. Current Technology

Biguanide and sulfonyl urea derivatives have been used as anti-diabetics so far. But these compounds have some drawbacks. For instance, biguanide compounds cause diabetic acidosis and sulfonyl urea compounds often cause hypoglycemia and it is required to be careful when taking these drugs.

Recently, thiazolidine-2,4-dione derivatives are reported to have blood glucose lowering activities. For example, Troglitazone (T. Yoshioka et al., J. Med. Chem. 1989, 32,421), Pioglitazone (H. Ikeda et al., J. Med. Chem. 1992, 35,2617) or Rosiglitazone (B. C. C. Cantello et al., J.Med. Chem. 1994, 37,3977) are mentioned as Thiazolidine-2,4dione derivatives and Troglitazone is applied for clinical use. However, these thiazolidine-2,4-dione compounds are reported to cause liver toxicity (R. Perfetti et al., Diabetes/Metabolism Review 1998,14(3),207) and further, side effects to troglitazone treatment have been reported. They include cardiomegaly and hepatic malfunction such as increase of amino trasferase (ATL), and lactic dehydrogenase (LDH) (R. R. Henry, Endocrinol.Metab,Clin,North AM. 1997,26,553).

To alleviate the side effect of thiazolidine-2,4-dione derivatives, several non-thiazolidine-2,4-diones are reported such as oxazoline-2,4-diones (R. L. Dow et al., J.Med.Chem. 1991,34,1538), 1-oxo-2,4-diazoline-3,5 dione (S. W. Goldstein et al., J.Med.Chem. 1993,36,2238), α-amino carboxylic acid (R. A. DeFronzo, Diabetes, 1988,37,677), and Dicarboxylic acid ester (H. Shinkai et al., J.Med.Chem. 1998,41,1927).

THE SUBJECT OF INVENTION

The present invention concerns ether and amide compounds which enhance insulin action and show hypoglycemic activity with low toxicities and a pharmaceutical composition containing these compounds as active ingredients.

A Solution to the Problem

After extensive research to make an anti-diabetic drug, the inventors found that new compounds, as shown by general formula (I), have potent anti-diabetic activities and fulfilled this invention.

Namely, the invention is the compounds as shown in general formula (I) and its pharmaceutically acceptable salts and a composition containing these compounds as active ingredients.

$$R_1—A—R_2 \quad (I)$$

wherein

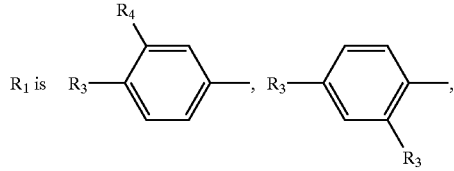

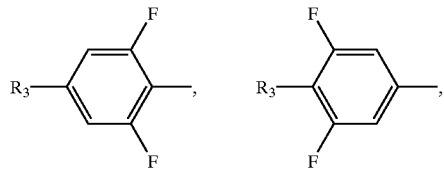

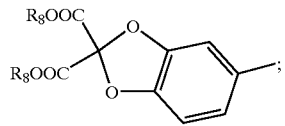

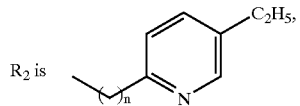

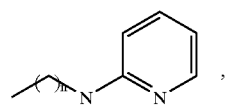

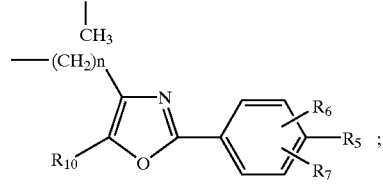

(with the provisos that (i) when A is —O—, then n is 2 or 3 (ii) when

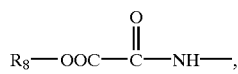

then n is 1 or 2. $R_3$ is OH—, $CH_3SO_2NH$—, $CF_3SO_2NH$—, $CH_3SO_2NHCH_2$—, $CF_3SO_2NHCH_2$—, HOOC—, $CH_3OOC$—,

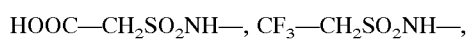

HOOC—$CH_2SO_2NH$—, $CF_3$—$CH_2SO_2NH$—,

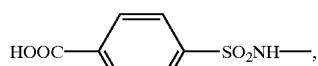

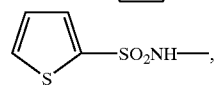

-continued

R$_8$—⟨C$_6$H$_4$⟩—SO$_2$NH—,

R$_8$—NHSO$_2$—,
R$_8$—NHSO$_2$—CH$_2$—, HOOC—CH$_2$—O—,
HSO$_3$N=CH—, or R$_9$—SO$_2$NHCO—;

R$_4$ is H, OH, O-alkyl or O—CH$_2$OCH$_3$;

R$_5$ is H, halogen atom, —CH$_2$COOH or OH;

R$_6$ and R$_7$ are hydrogen, t-butyl or pyrolidyl;

R$_8$ is hydrogen or lower alkyl;

R$_9$ is alkyl or thienyl;

R$_{10}$ is lower alkyl)

EXAMPLES OF INVENTION 70 compounds are exemplified as follows, but the invention is not limited to these compounds. Further the preparation of the compounds 1–70 are exemplified in each experimental sections.

(Compound 1)

CH$_3$SO$_2$NH—⟨C$_6$H$_4$⟩—O—CH$_2$CH$_2$—⟨oxazole, CH$_3$⟩—C$_6$H$_5$ (Compound 2)

CF$_3$SO$_2$NH—⟨C$_6$H$_4$⟩—O—CH$_2$CH$_2$—⟨oxazole, CH$_3$⟩—C$_6$H$_5$ (Compound 3)

HOOC—CH$_2$—SO$_2$NH—⟨C$_6$H$_4$⟩—O—CH$_2$CH$_2$—⟨oxazole, CH$_3$⟩—C$_6$H$_5$ (Compound 4)

CH$_3$—⟨C$_6$H$_4$⟩—SO$_2$NH—⟨C$_6$H$_4$⟩—O—CH$_2$CH$_2$—⟨oxazole, CH$_3$⟩—C$_6$H$_5$ (Compound 5)

HOOC—⟨C$_6$H$_4$⟩—SO$_2$NH—⟨C$_6$H$_4$⟩—O—CH$_2$CH$_2$—⟨oxazole, CH$_3$⟩—C$_6$H$_5$ (Compound 6)

C$_6$H$_5$—SO$_2$NH—⟨C$_6$H$_4$⟩—O—CH$_2$CH$_2$—⟨oxazole, CH$_3$⟩—C$_6$H$_5$ (Compound 7)

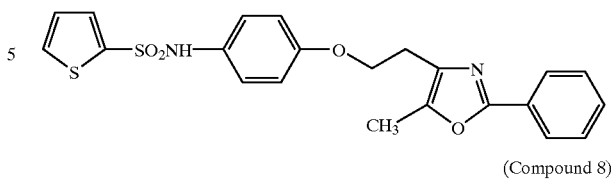

(Compound 8)

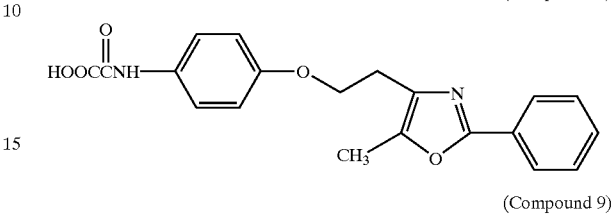

(Compound 9)

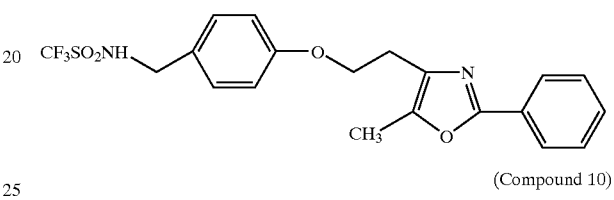

(Compound 10)

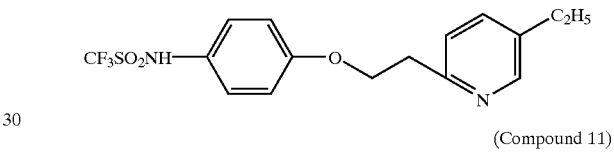

(Compound 11)

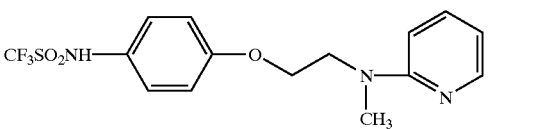

(Compound 12)

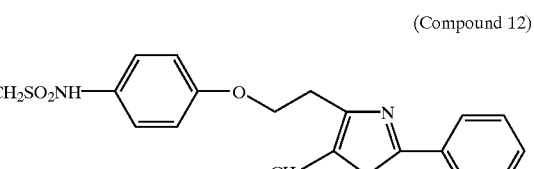

(Compound 13)

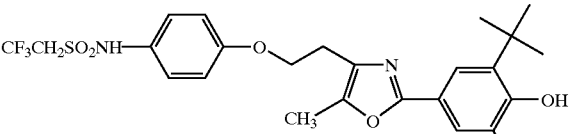

(Compound 14)

(Compound 15)

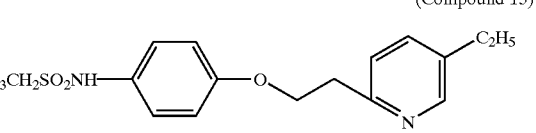

-continued
(Compound 16)
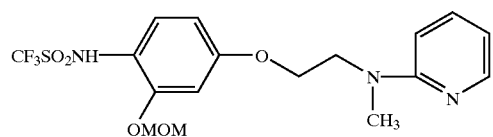
(Compound 17)
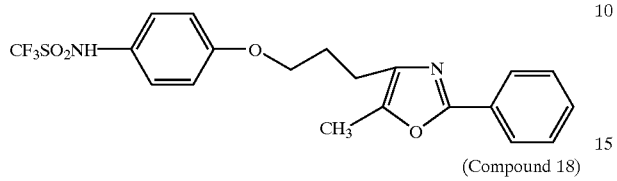
(Compound 18)
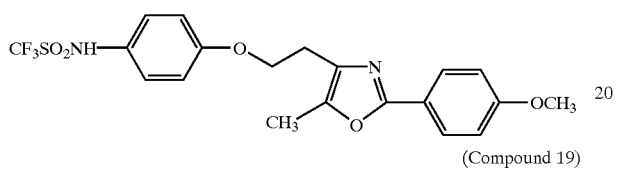
(Compound 19)
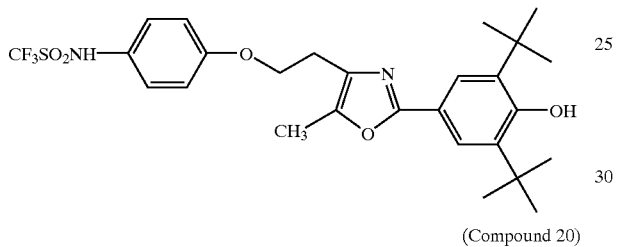
(Compound 20)
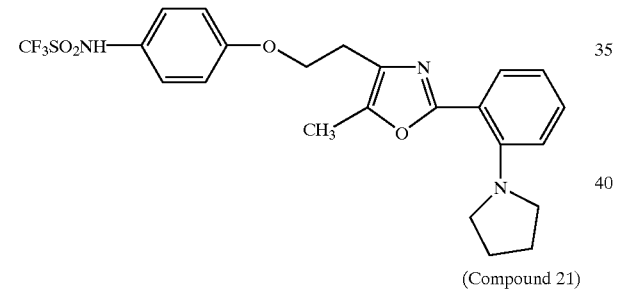
(Compound 21)
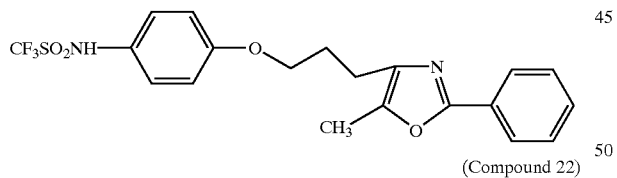
(Compound 22)
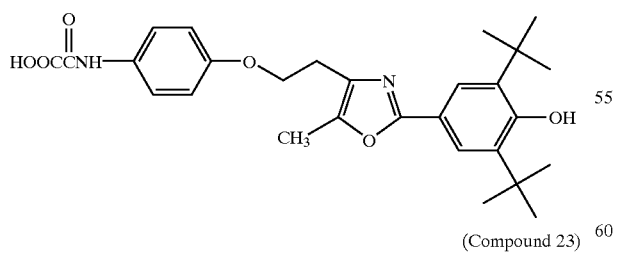
(Compound 23)
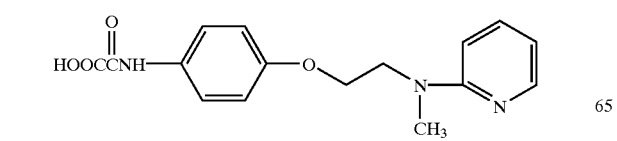
-continued
(Compound 24)
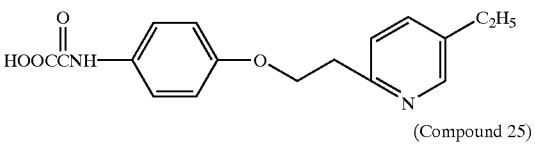
(Compound 25)
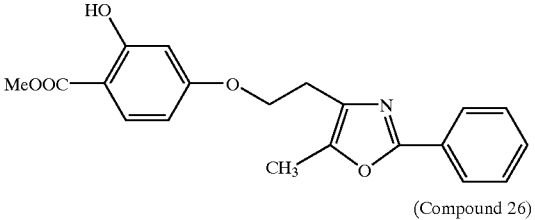
(Compound 26)
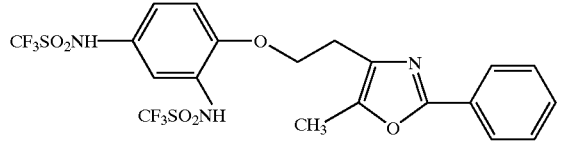
(Compound 27)
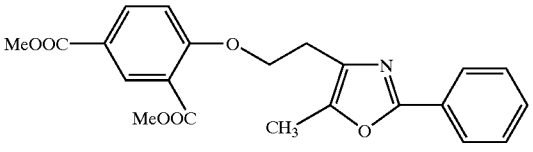
(Compound 28)
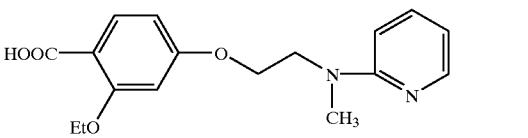
(Compound 29)
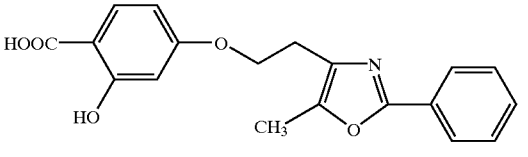
(Compound 30)
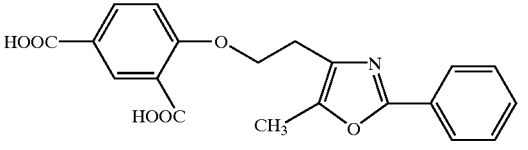
(Compound 31)
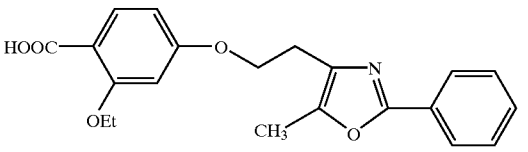
(Compound 32)
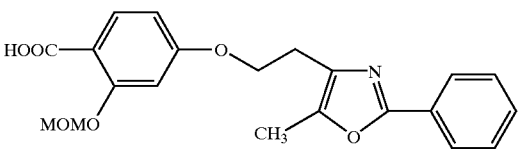

(Compound 33)
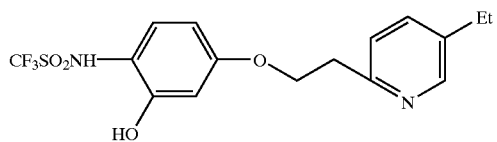
(Compound 34)
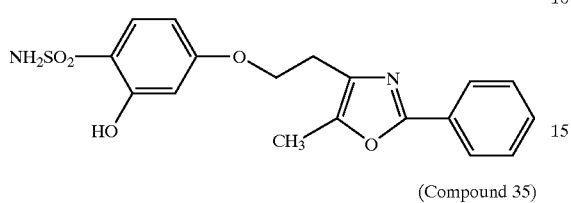
(Compound 35)
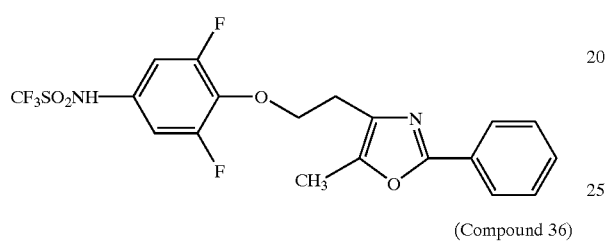
(Compound 36)
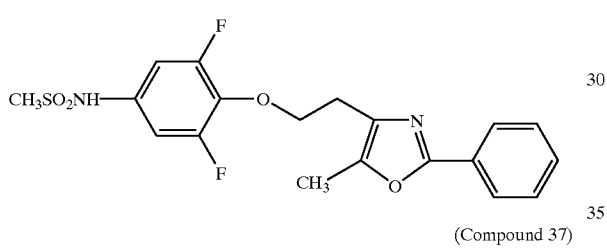
(Compound 37)
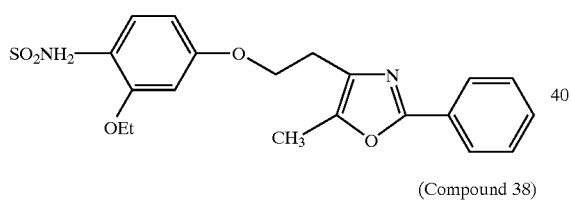
(Compound 38)
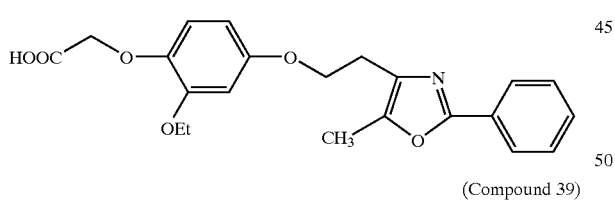
(Compound 39)
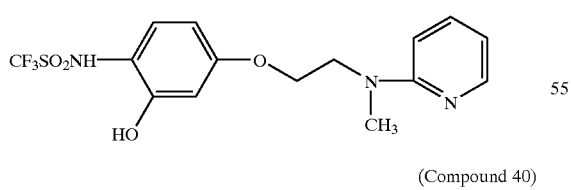
(Compound 40)
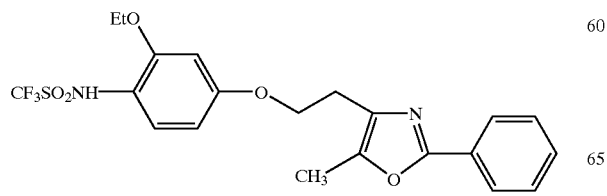
(Compound 41)
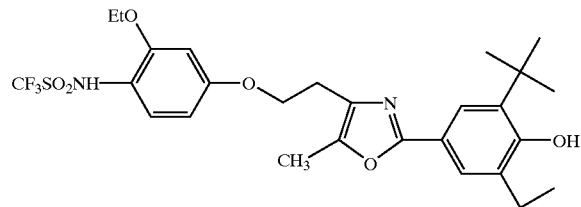
(Compound 42)
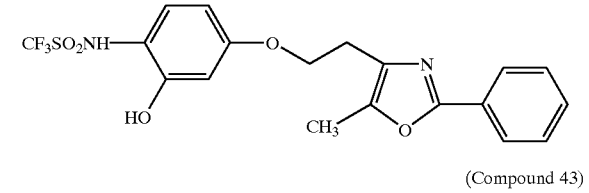
(Compound 43)
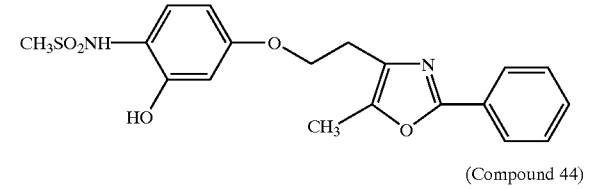
(Compound 44)
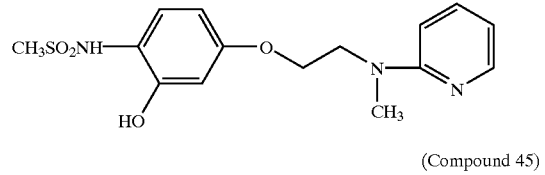
(Compound 45)
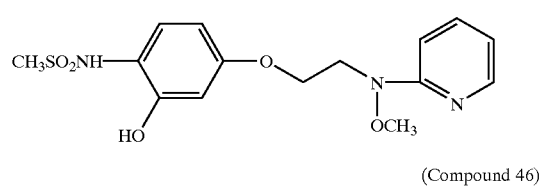
(Compound 46)
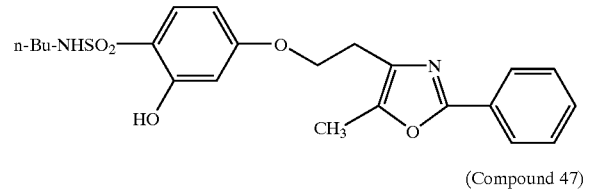
(Compound 47)
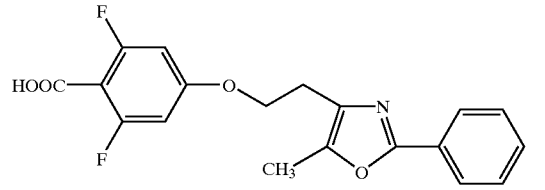
(Compound 48)
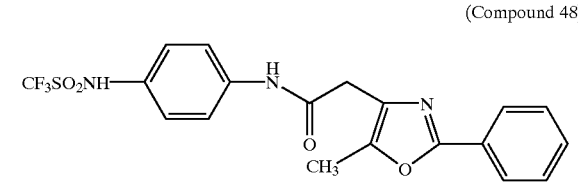

(Compound 49)
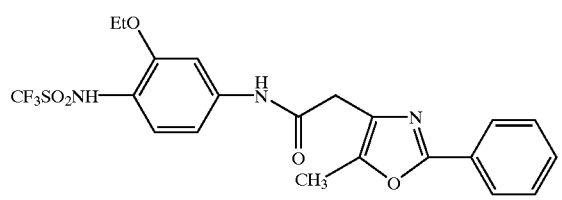
(Compound 50)
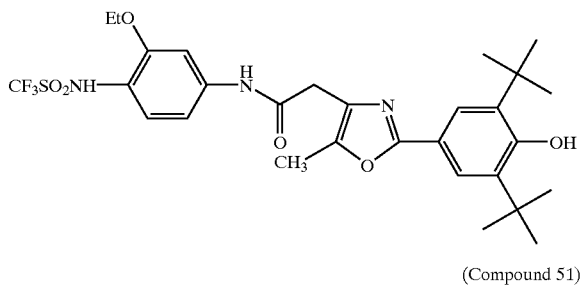
(Compound 51)
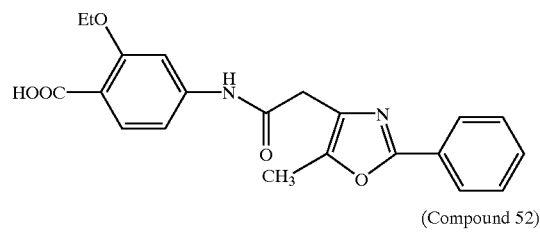
(Compound 52)
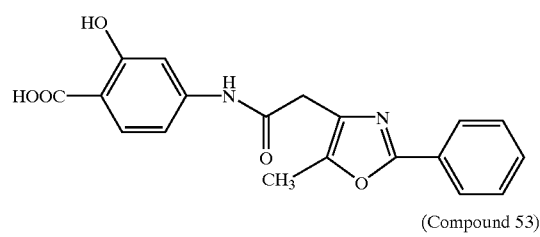
(Compound 53)
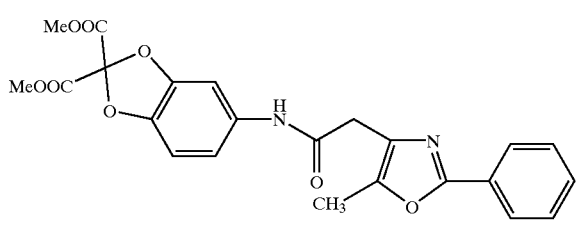
(Compound 54)
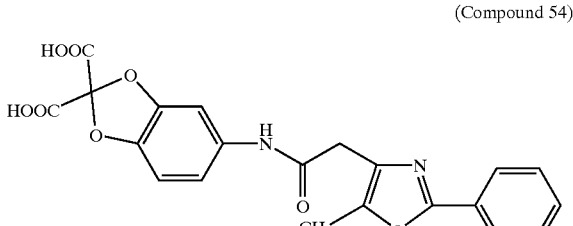
(Compound 55)
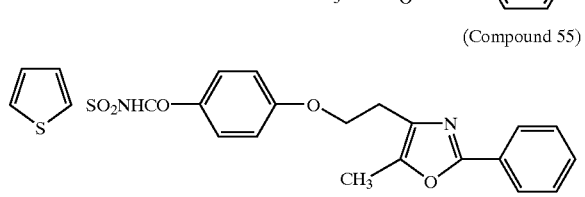
(Compound 56)
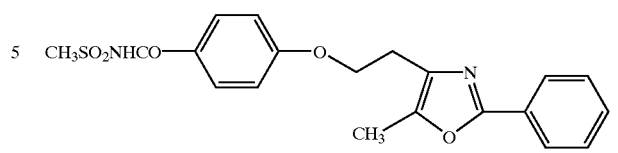
(Compound 57)
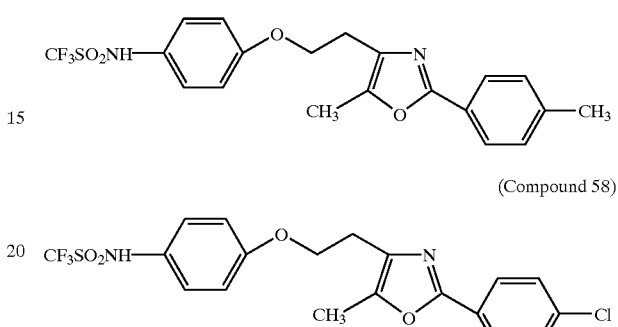
(Compound 58)
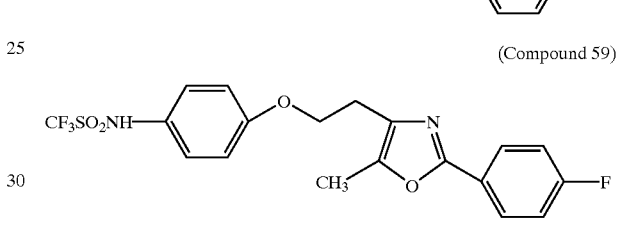
(Compound 59)
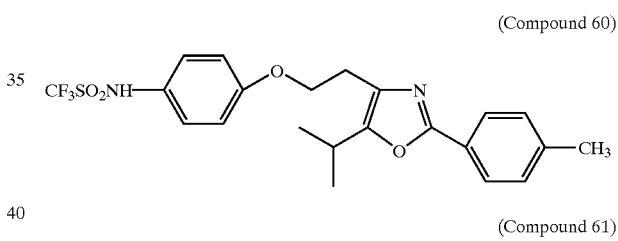
(Compound 60)
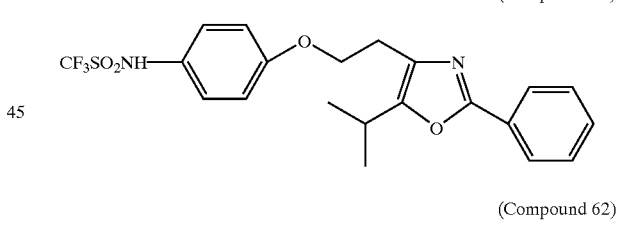
(Compound 61)
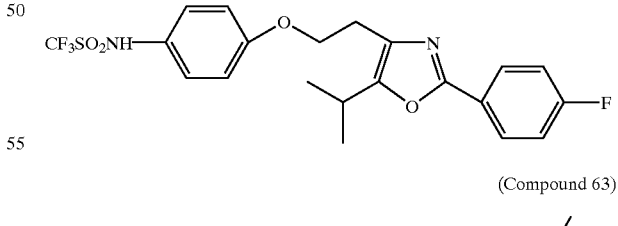
(Compound 62)
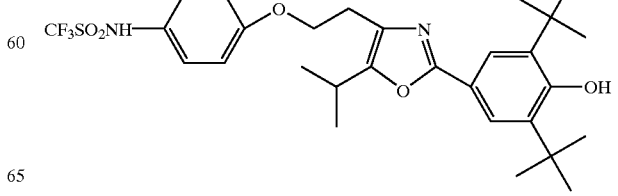
(Compound 63)

-continued (Compound 64)
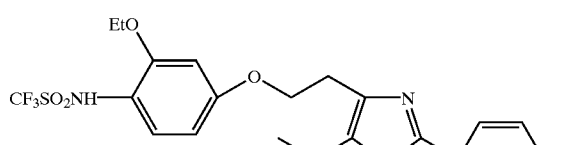

(Compound 65)
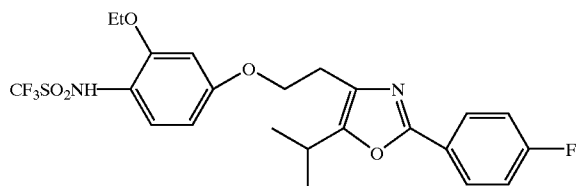

(Compound 66)
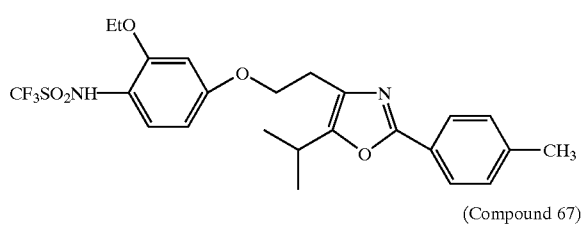

(Compound 67)
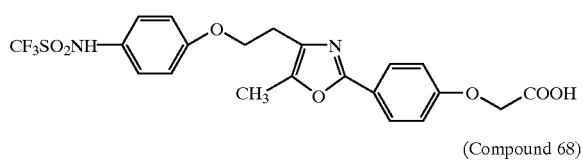

(Compound 68)
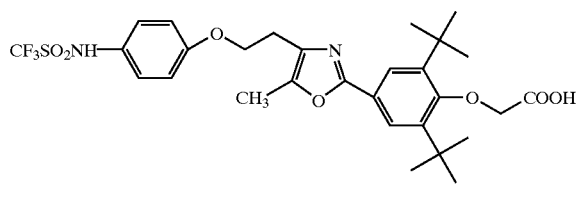

(Compound 69)
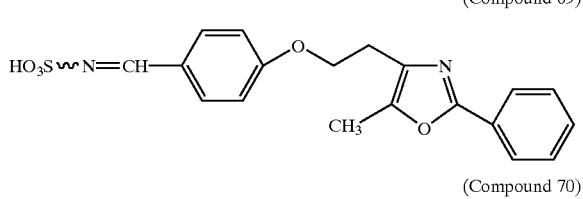

(Compound 70)
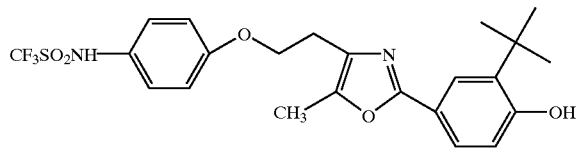

Typical preparations of the compounds of general formula (I) according to the invention are shown.

(I) The preparation of a compound of general formula (I) in which

A is —O—;

$R_2$ is 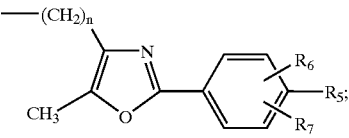

(wherein: $R_5$, $R_6$, and $R_7$ have the above-mentioned meanings; n=2)

(a) In case of $R_1$ is $R_3$— 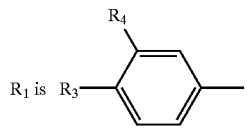

in which $R_3$ is $CH_3SO_2NH$— or $CF_3SO_2NH$— and $R_4$ is H.

The compounds can be obtained by means of the following reaction diagram: Asparatic acid β-methyl ester (2) (J.Arg.Chem.Soc.Japan, 1951–1952,25,129): (C.A.47,6065i or R. L. Prestige et al., J.Org.Chem. 1975,40,3287) as a starting material is converted to compound (3) by the known method (B. Helvin et al.,J.Med.Chem. 1992,35.1853) and compound (3) is tosylated or mesylated to obtain compound (4). The coupling reaction of compound (4) with nitrophenol yields compound (5) and then compound (5) is reduced with $H_2$—Pd/C to obtain compound (6) and compound (6) is subjected to reaction with sulfonyl chloride (7) or sulfonic acid anhydride (8) to obtain the compound of general formula (I).

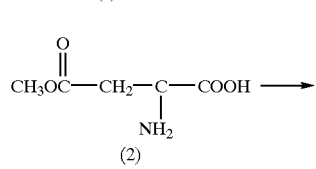
(2)

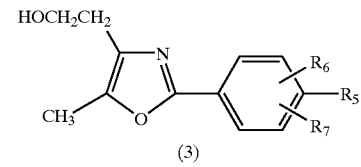
(3)

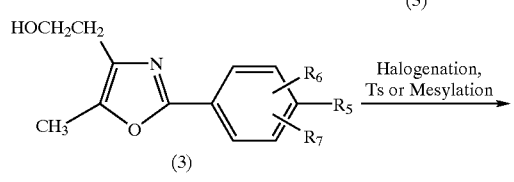
(3)

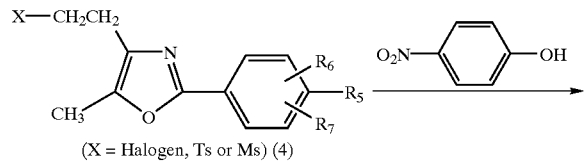
(X = Halogen, Ts or Ms) (4)

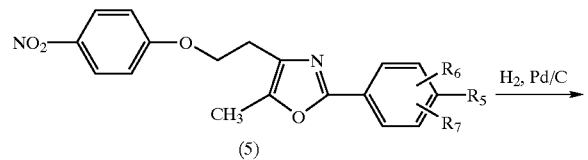
(5)

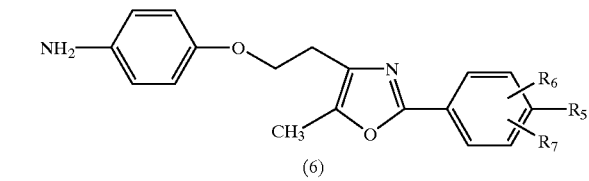
(6)

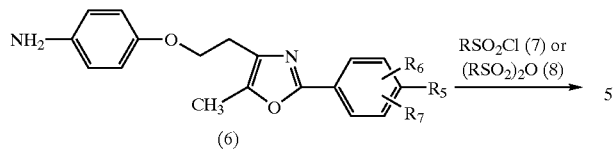

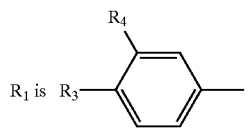

in which $R_3$ is $HOOCCH_2SO_2NH$— and $R_4$ is H.

The compounds can be obtained by mean of the following reaction diagram:

The reaction of compound (6) and $EtOOC.CH_2SO_2Cl$ as a sulfonyl chloride, namely $CH_3OOCH_2SO_3Cl$ (9), yields the ester (11) and then compound (11) is hydrolyzed to obtain the compound of general formula (I).

The above mentioned compound (9) is obtained by the chlorination of sulfoacetic acid ($HOOCCH_2SO_3H$(10)) with $SOCl_2$ and then reacted with alcohol (R. L. Hinman et al. (J.Am.Chem. Soc. 1959,81,5655), (H. T. Lee et al., Bioorg.Med.Chem.Lett.1998,8,289)

(b) In case of

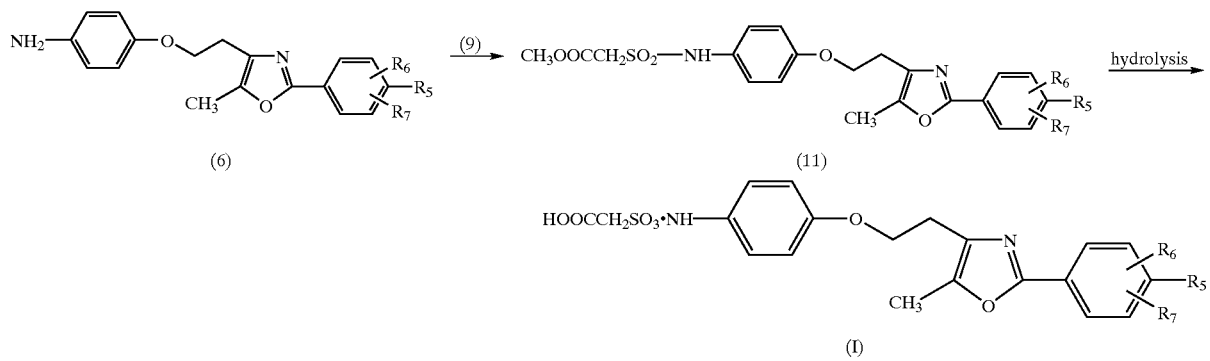

(c) In case of

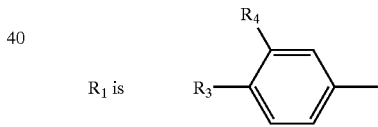

in which $R_3$ is HOOC—CONH— and $R_4$ is H.

The compound can be obtained by means of the following reaction diagram:

The reaction of compound (6) and methyloxalate yields compound (12) and compound (12) is hydrolyzed to obtain the compound of general formula (I). Further compound (12) is N-alkylated with alkylhalide and then subjected to hydrolysis to obtain the compound of general formula (I).

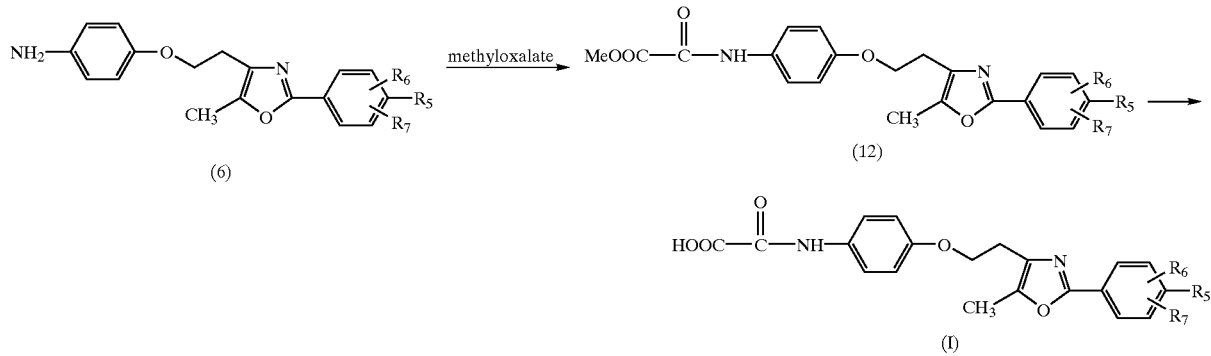

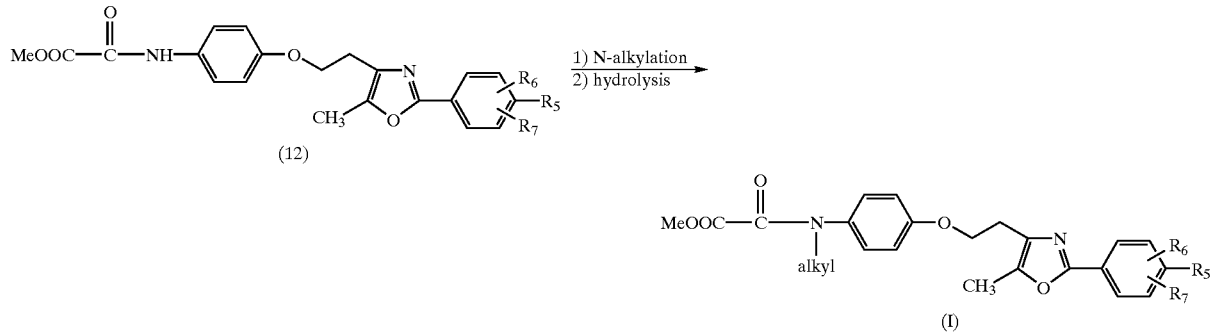

(d) In case of

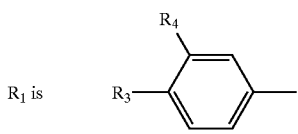

R₁ is in which R₃ is CH₃SO₂NHCH₂—, CF₃SO₂NHCH₂—and HOOC—CONH—, and R₄ is H.

The compound can be obtained by means of the following reaction diagram:

Compound (4) is reacted with p-hydroxy benzaldehyde to obtain compound (13) and compound (13) is subjected to reductive amination using benzylamine and sodium borohydride to obtain compound (14).

After debenzylation of compound (14) in H₂—Pd/C, compound (15) is obtained. Compound (15) is reacted with sulfonyl chloride, sulfonic acid anhydride, EtOOC.CH₂SO₂Cl or methyloxalate as the same manner as in case of compound (6) and compound (12), then the compound of general formula (I) is obtained.

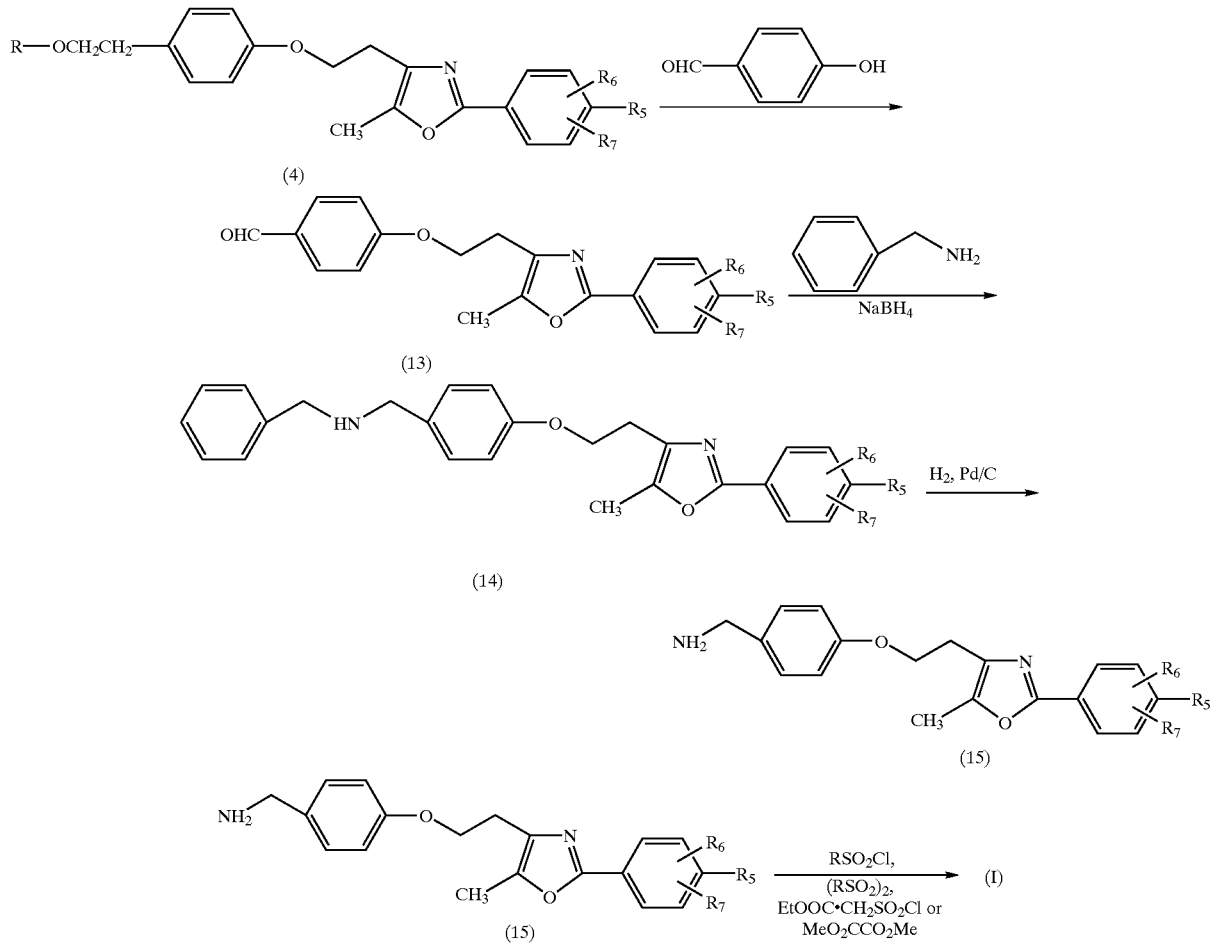

R=Tosyl or mesyl (e) In case of $R_1$ is 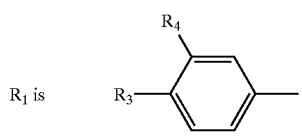

in which $R_3$ is HOOC— or $CH_3OOC$— and $R_4$ is —OH or —O-alkyl.

As shown in the following reaction diagram, compound (32) and compound (3) is subjected to the MITSUNOBU reaction to obtain the compound (33) which is the compound of general formula (I).

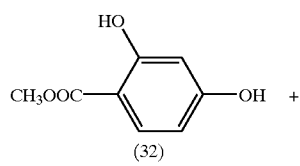
(32)

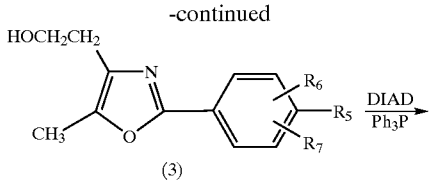
(3)

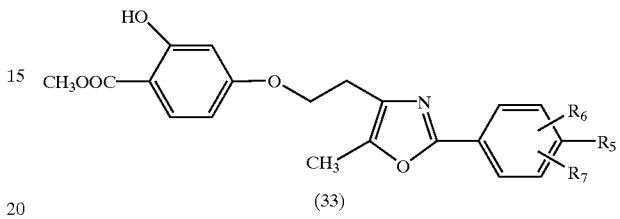
(33)

Further, compound (33) can be converted to compound (34) and compound (36) as shown in the following diagram.

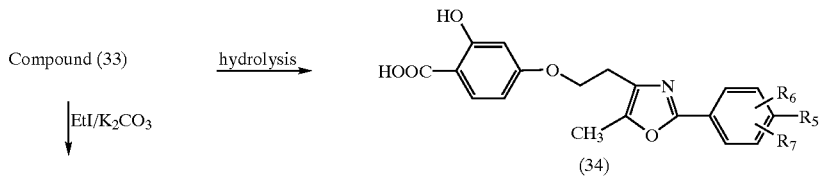
(34)

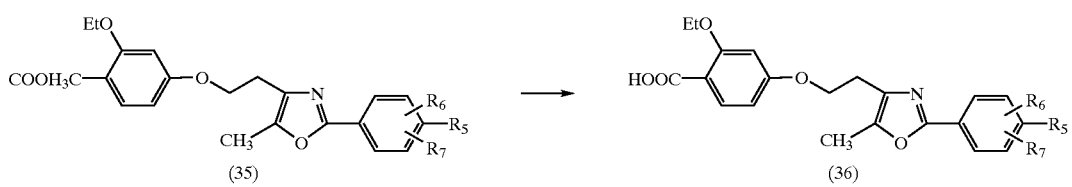
(35) → (36)

(f) In case of $R_1$ is 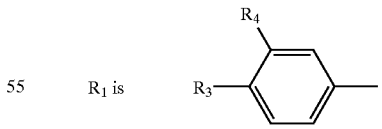

in which $R_3$ is $NH_2SO_3$— or alkyl-$NHS_2$— and $R_4$ is —OH.

As shown in the following reaction diagram, according to the literature method (J.Med.Chem.1997,20, 1235), compound (51) and (52) are obtained from resorcin dimethyl ether (50).

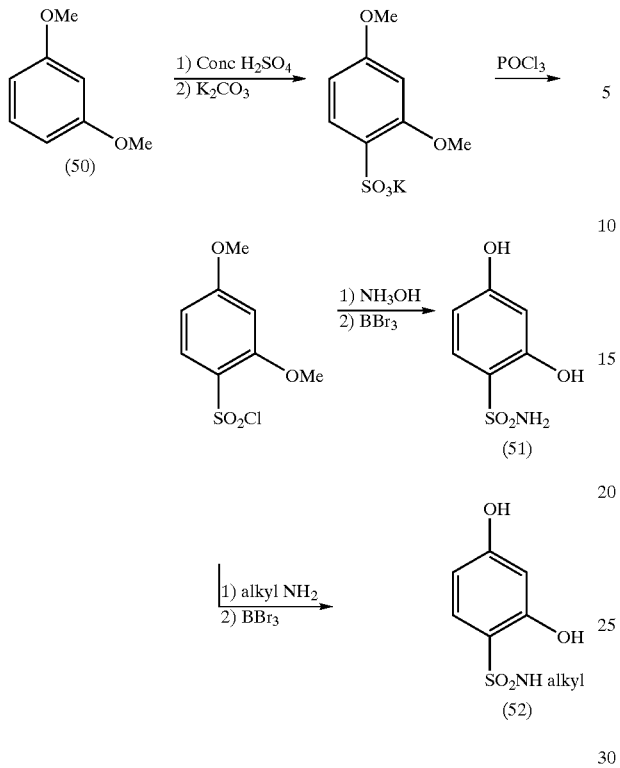

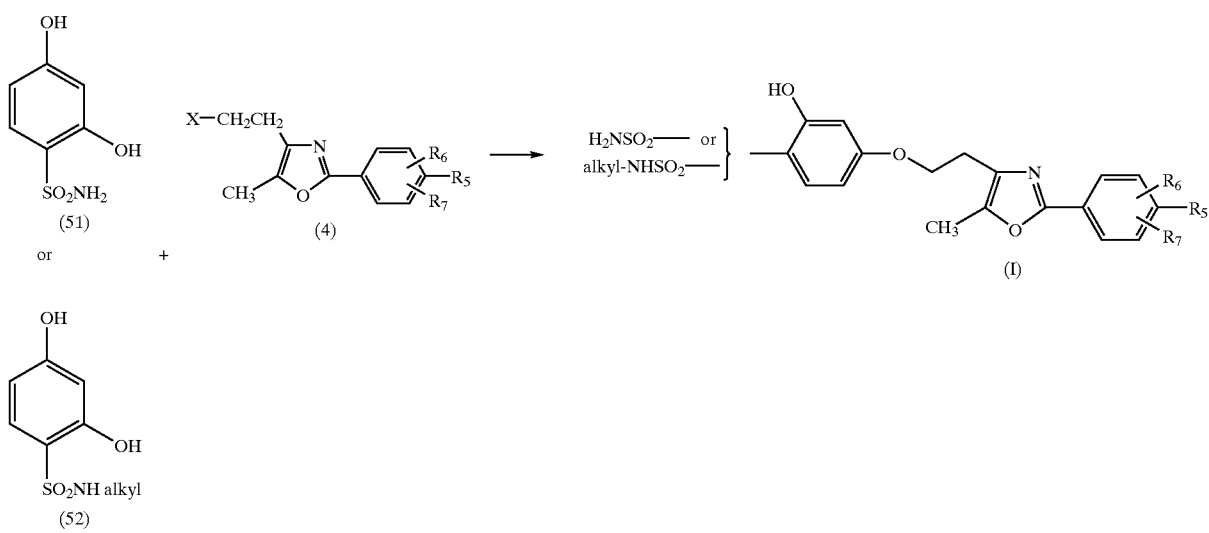

Further, obtained compounds (51) and (52) are reacted with compound (4) to obtain general formula (I) as follows.

(g) In case of $R_1$ is 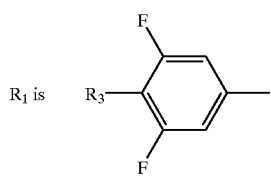

in which $R_3$ is $CH_3SO_2NH-$ or $CF_3SO_2NH-$.

As shown in the following reaction diagram, compound (53) is subjected to the MITSUNOBU reaction to obtain compound (54) and reduction of compound (54) yields compound (55). Compound (55) is converted to compound (56) according to the method of the preparation of compound (42) from compound (39).

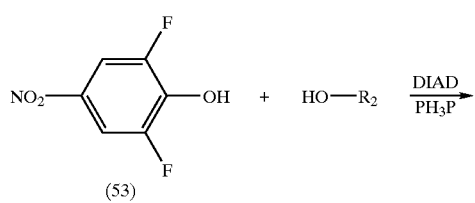

(53)

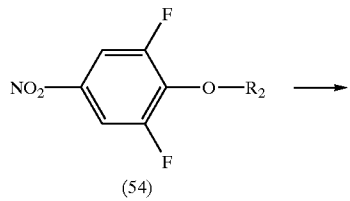

(54)

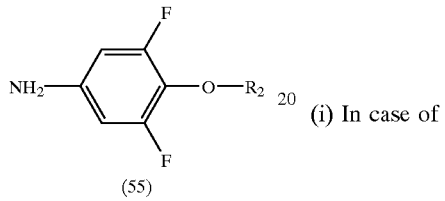

(55)

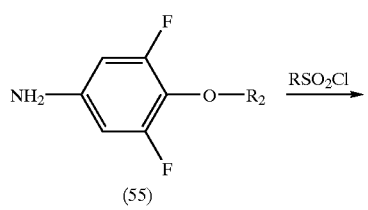

(55)

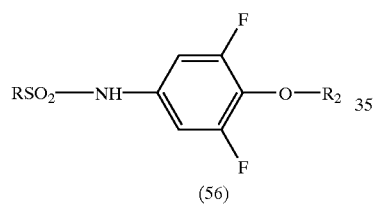

(56)

(h) In case of

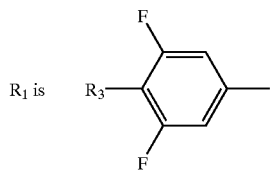

in which $R_3$ is —COOH.

As shown in the following reaction diagram, compound (57) is reacted with compound (4) and obtain the ether compound (58) and the resulting compound (58) is hydrolyzed to obtain compound (59) which is the compound of general formula (I).

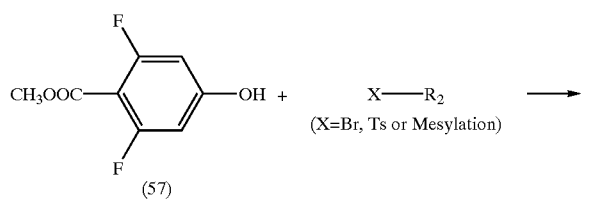

(57)

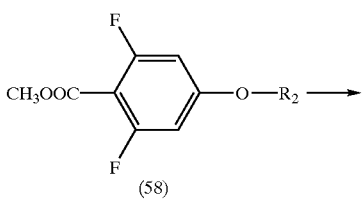

(58)

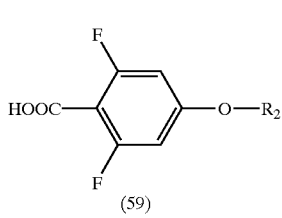

(59)

(i) In case of $R_1$ is 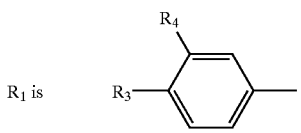

in which $R_3$ is $MeOOCCH_2$—, and $R_4$ is —O-alkyl.

As shown in the following reaction diagram, compound (61), which is obtained from compound (60), is reacted with compound (4) to obtain the compound of general formula (I).

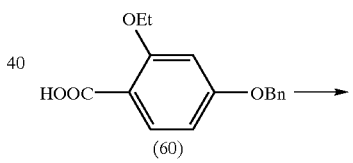

(60)

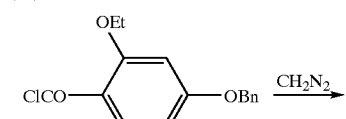

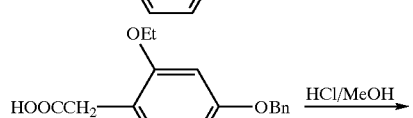

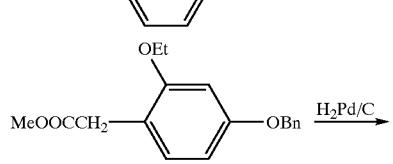

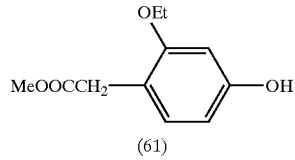

(61)

(61) + (4) ⟶

-continued

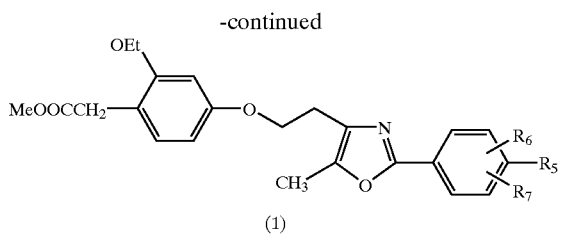
(1)

(j) In case of

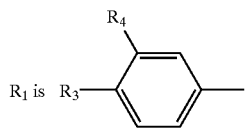

in which $R_3$ is $NH_2SO_2CH_2$— or alkyl-$NHS_{O2}CH_2$— and $R_4$ is OH or —O-alkyl.

As shown in the following reaction diagram, after reduction of compound (62), the obtained compound (63) is reacted with $Na_2SO_3$ to obtain compound (64) according to the reported method (J.C.S.Chem.Comom.,1989,521). Then compound (64) is chlorinated with $POCl_3$ and treated with aqueous $NH_3$ to obtain the amide compound (65). After debenzylation of compound (65), compound (66) is obtained. Compound (66) is reacted with compound (4) to yield the compound of general formula (I).

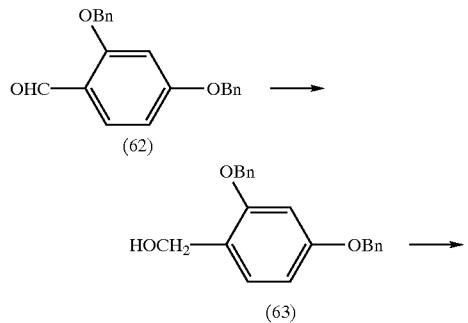

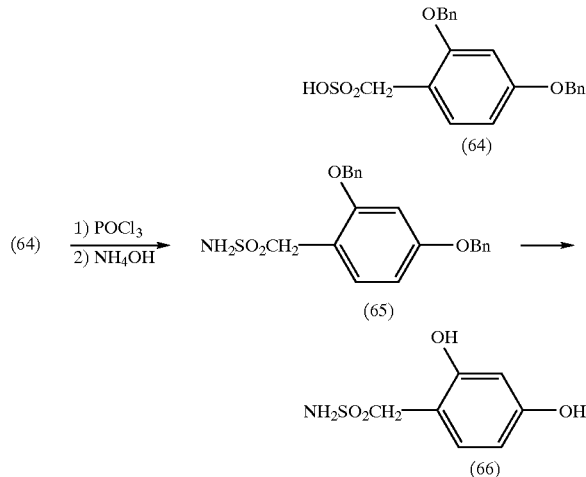

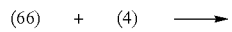

-continued

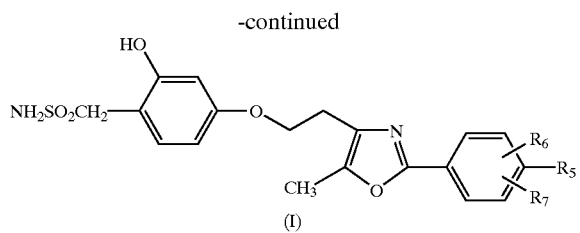
(I)

(II) The preparation of a compound of general formula (I) in which

A is —O—;

$R_2$ is

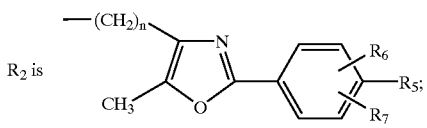

(wherein: $R_5$, $R_6$, and $R_7$ have the above mentioned meaning; n=3)

(a) In case of

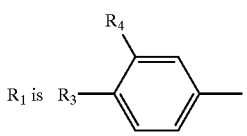

in which $R_3$ is $CH_3SO_2NH$— or $CF_3SO_2NH$—, and $R_4$ is H.

As shown in the following reaction diagram, glutamic acid γ-methyl ester (16) is used in stead of aspartic acid β-methyl ester (2). Compound (17) is obtained from compound (16) by the same method as compound (3) is obtained from compound (2).

After compound (17) is halogenated, tosylated or mesylated, obtained compound (18) is coupled with nitrophenol and the resulting compound (19) is hydrogenated to obtain compound (20). The obtained compound (20) is reacted with one of sulfonyl chlorides, sulfonic acid anhydrides, $EtOOC.CH_2SO_2Cl$ or methyloxalate to obtain the compound of general formula (I).

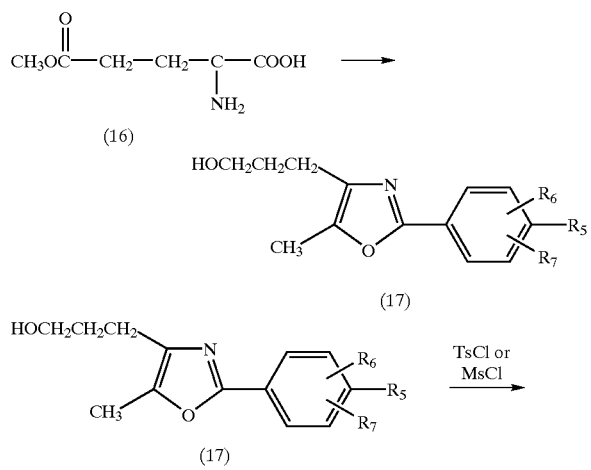

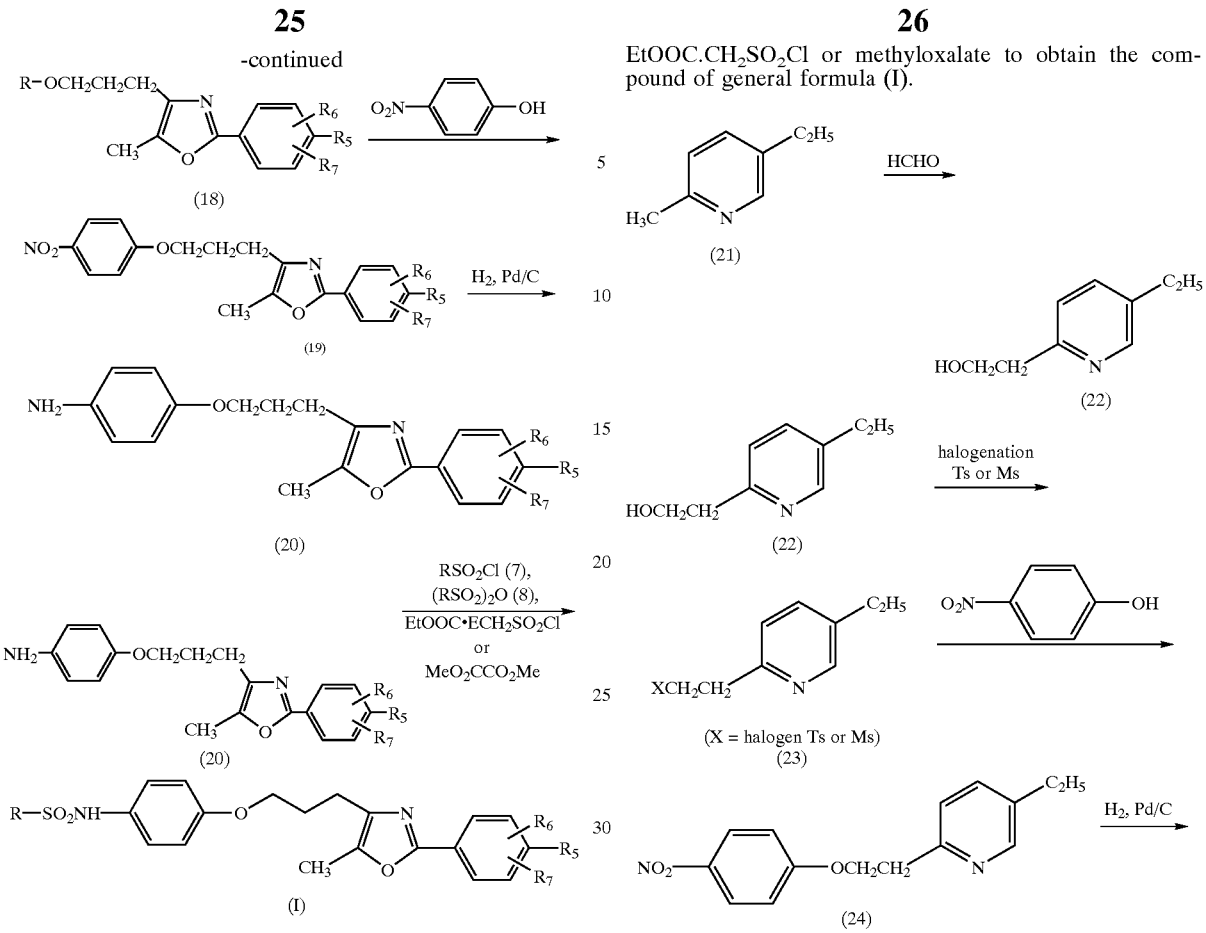

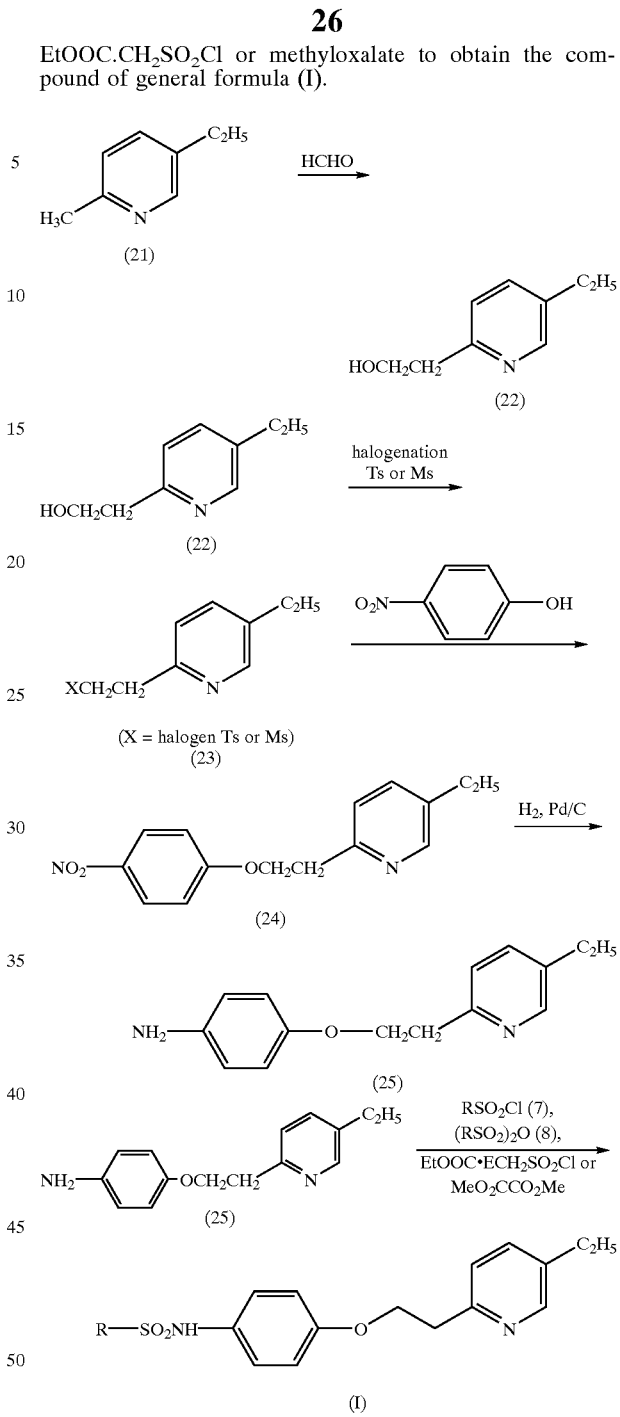

(II) The preparation of a compound of general formula (I) in which

A is —O—;

$R_2$ is —$(CH_2)_2$—

(a) In case of

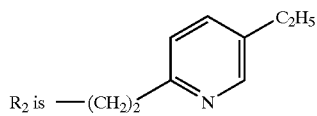

in which $R_3$ is $CH_3SO_2NH$— or $CF_3SO_2NH$—, and $R_4$ is H.

As shown in the following reaction diagram, after the reaction of 2-methyl 5-ethylpyridine (21) and formaldehyde using the reported method (Japanese Patent Publication, 1981-65870), compound (22) is obtained. After compound (22) is halogenated, tosylated or mesylated, obtained compound (23) is coupled with nitrophenol and the resulting compound (24) is hydrogenated to obtain compound (25), by the same method as compound (4) is obtained from compound (3).

The obtained compound (25) is reacted with several sulfonylchlorides (7), sulfonic acid anhydrides (8), EtOOC.CH$_2$SO$_2$Cl or methyloxalate to obtain the compound of general formula (I).

(b) In case of

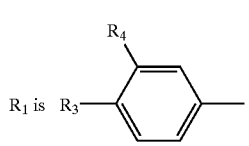

in which $R_3$ is $CH_3SO_2NH$— or $CF_3SO_2NH$—, and $R_4$ is —OH or —O-alkyl.

As shown in the following reaction diagram, compound (37) is reacted with HO—$R_2$ to obtain compound (38) and compound (38) is hydrogenated to compound (39), or compound (38) is alkylated to compound (40) and reduction of compound (40) yields compound (41). The compound (39) or (41) is reacted with $RSO_2Cl$ to obtain compound (42) or compound (43).

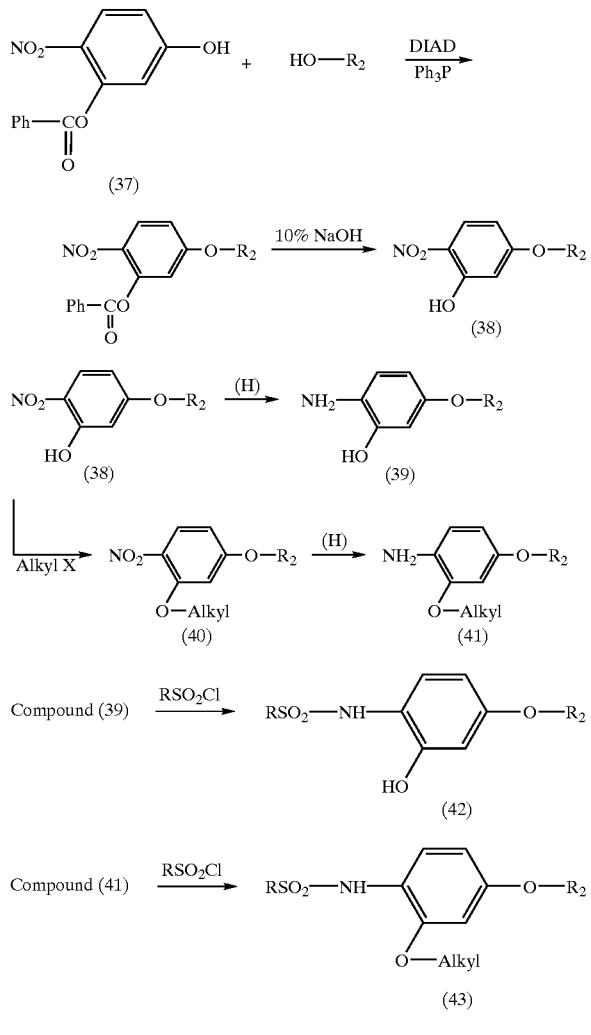

Compound (37) in the diagram can be obtained from resorcin as follow.

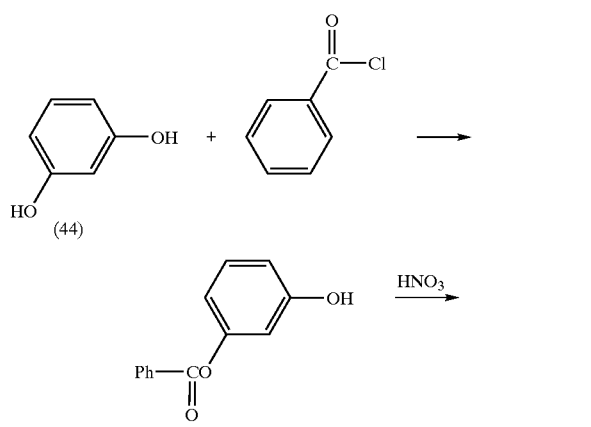

-continued

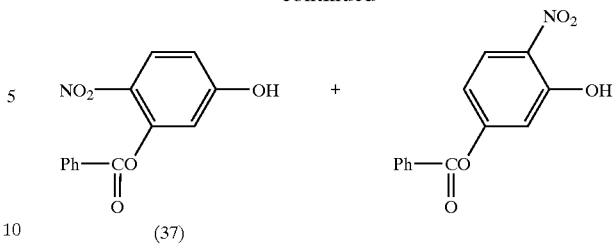

And compound (42) and (43) can be obtained by using the reported method of coupling reaction of fluorobenzene and alcohol (Bioorg.Med.Chem.Lett.,1994,4 (10),1181). Namely, 2-OMOM (methoxy methyl)-4-fluoro nitrobenzene (45) is reacted with HO—$R_2$ to give compound (46) and resulting compound (46) is reduced to obtain compound (47).

Compound (47) is reacted with $RSO_2Cl$ to obtain compound (48) and after deprotection of MOM-group in compound (48), compound (42) is obtained.

Instead of compound (45), compound (49) is also converted to compound (41), and compound (43) is obtained from compound (41) by the same method as compound (48) is obtained from compound (46).

The process is shown in the following reaction diagram.

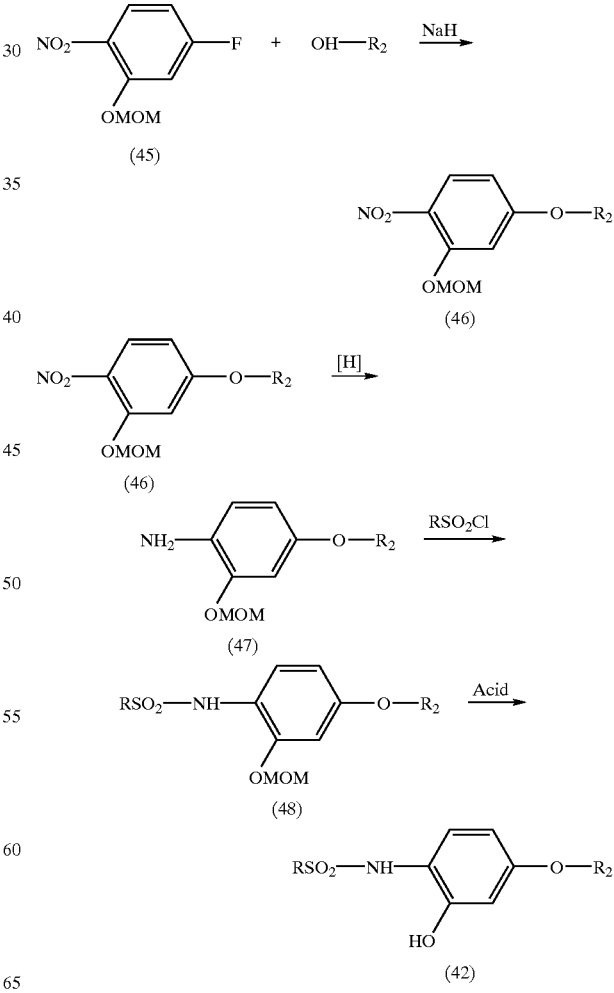

(IV) The preparation of a compound of general formula (I) in which

A is —O—;

R₁ is —(CH₂)₂—N(CH₃)-(2-pyridyl)

(a) In case of

R₁ is (aryl with R₃, R₄)

in which R₃ is CH₃SO₂NH— or CF₃SO₂NH—, and R₄ is —H.

As shown in the following reaction diagram, compound (28), obtained from 2-chloropyridine (26) or 2-methyl amino pyridine (27), is tosylated or mesylated to obtain compound (29). Compound (29) is subjected to coupling reaction with nitro phenol and obtained compound (30) using the same manner to obtain compound (3). Resulting compound (30) is reduced to obtain compound (31) and compound (31) is reacted with sulfonyl chlorides (7), sulfonic acid anhydrides (8), EtOOC.CH₂SO₂Cl and methyloxalate to obtain the compound of general formula (I).

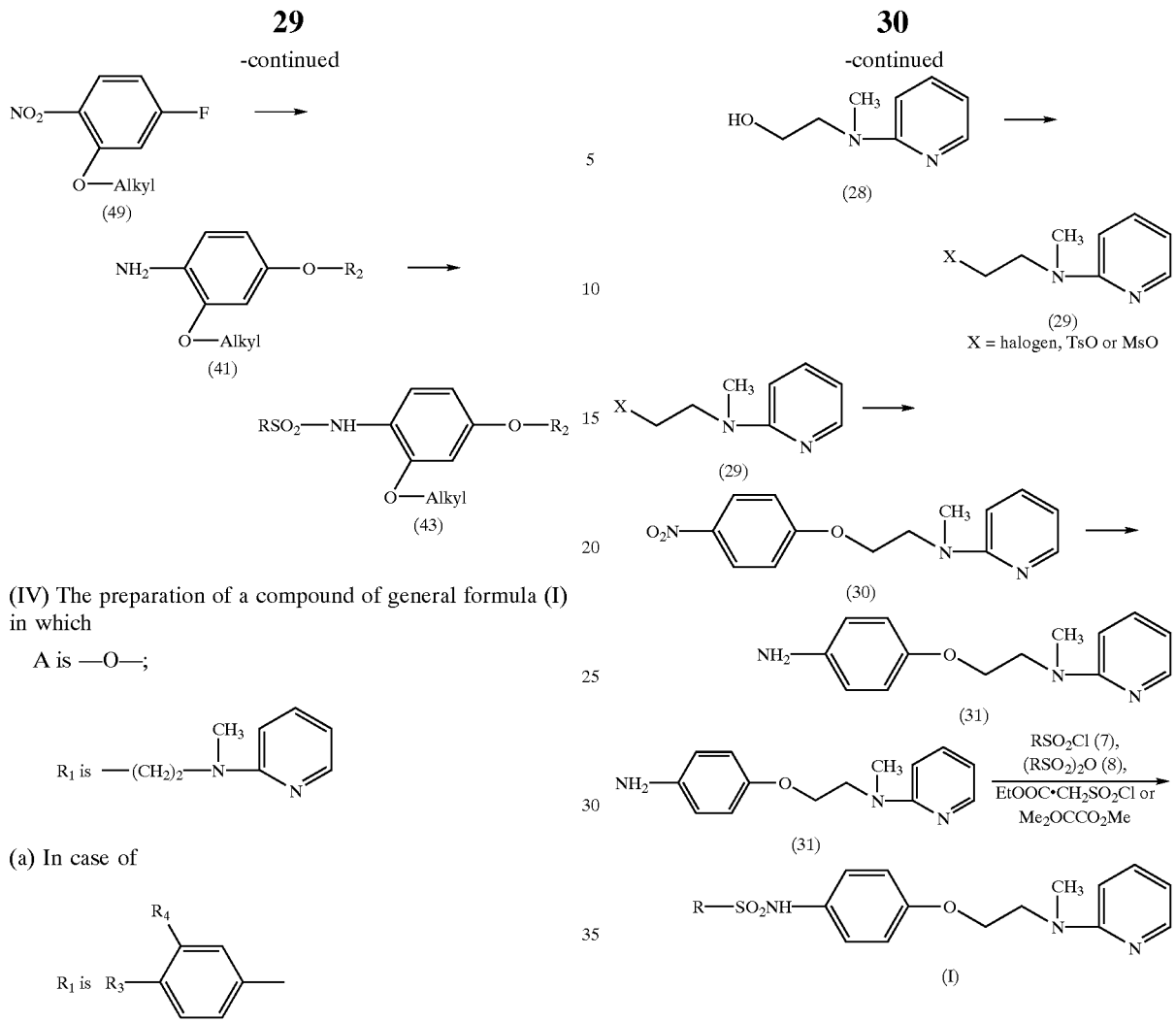

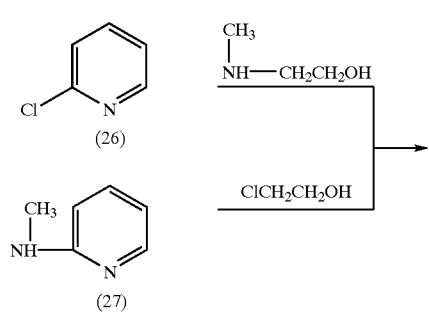

(V) The preparation of a compound of general formula (I) in which

A is —NH—CO—

(a) In case of

R₁ is (aryl with R₃, R₄)

in which R₃ is CH₃SO₂NH— or CF₃SO₂NH—, and R₄ is —H.

As shown in the following reaction diagram, compound (67), intermediate for compound (3), is obtained according to the reported method (J.Med.Chem.1999,35,1853) and compound (67) is hydrolyzed to obtain compound (68). After chlorination of compound (68), obtained chloride is reacted with p-nitroaniline to obtain compound (69).

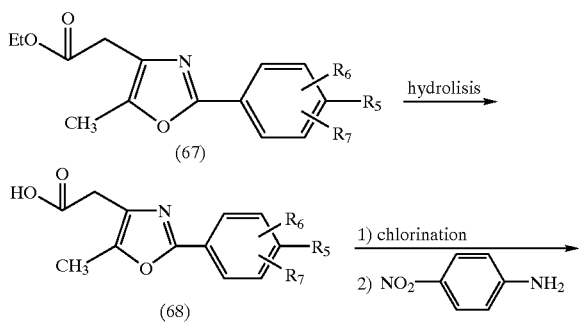

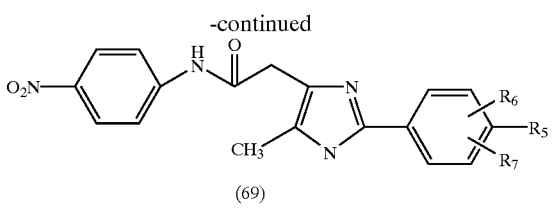

Then compound (69) is hydrogenated to obtain compound (70) according to the same method used to prepare compound (5). Compound (70) is reacted with sulfonyl chlorides (7), sulfonic acid anhydrides (8), $EtOOC \cdot CH_2SO_2Cl$ and methyloxalate to obtain the compound of general formula (I).

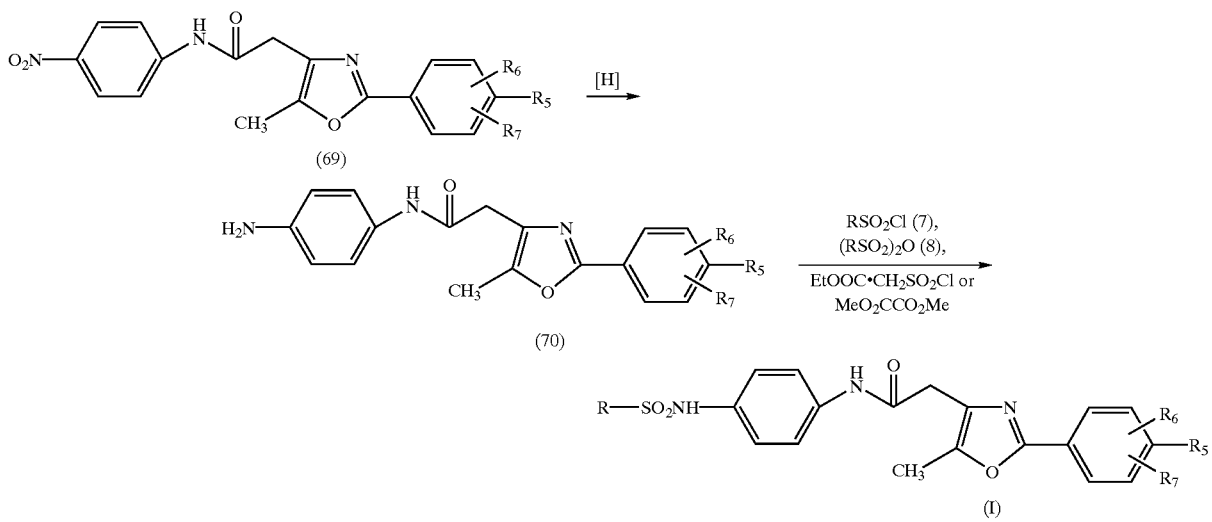

(b) In case of $R_1$ is $$\begin{array}{c} R_4 \\ R_3 - \phantom{X} - \end{array}$$

in which $R_3$ is $R_9SO_2NHCO-$ ($R_9$=alkyl or thienyl), and $R_4$ is H.

As shown in the following reaction diagram,
carboxylic acid of compound (71) is reacted with CDI (Carbonyl Diimidazole) and then subjected to react with sulfamine of compound (72) in the presence of DBU (1,8-Diazabicyclo[5,4,0]undeca-7-ene) and obtain the compound of general formula (I). (Bioorg.Med.Chem. Lett.1995,1155)

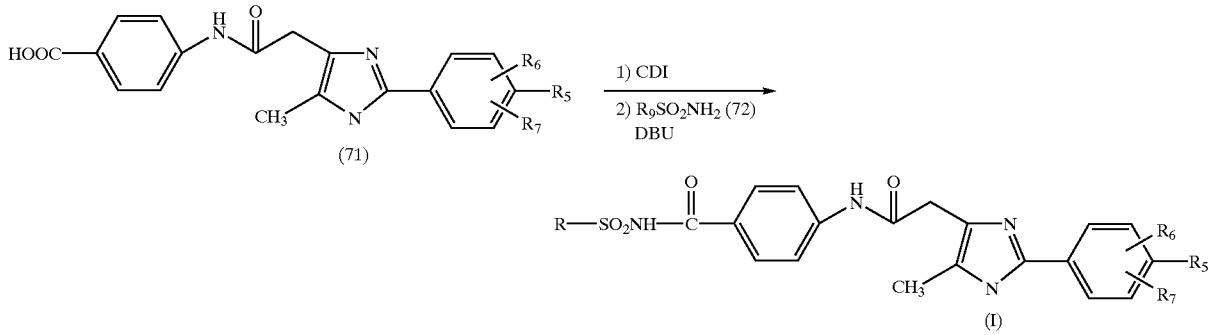

As pharmaceutical acceptable salts of a compound of general formula (I), sodium salt, potassium salt and inorganic base are mentioned.

In case of $R_1$ containing pyridine base, salts of inorganic and organic acids are mentioned. As the salt of inorganic acid, hydrochloride and sulfate are mentioned. As the salt of organic acid, acetate succinate and fumarate are mentioned.

A compound of general formula (I) can be used itself or formulated to pharmaceutical product such as powder, granule, tablet and capsule by known pharmaceutical technology.

Pharmacological Experiment

Hypoglycemic Activity in Mice

Test compounds were suspended in 0.5% Methyl cellulose solution and administrated (p.o.) to db/db mice (obtained from Nihon Clea) at a range of 3–30 mg/kg once a day for four consecutive days. Troglitazone (300 mg/kg) was also administrated for control. The results are shown in Table 1.

The compound number corresponds to the experimental number.

TABLE 1

| Compound No. | Dosage (mg/kg) | Hypoglycemic activity (%) |
|---|---|---|
| 1 | 30 | 24.6 |
| 2 | 10 | 49.0 |
| 8 | 10 | 26.0 |
| 9 | 10 | 24.0 |
| 10 | 10 | 32.4 |
| 11 | 10 | 15.4 |
| 18 | 10 | 34.7 |
| 19 | 10 | 12.8 |
| 21 | 10 | 34.6 |
| 24 | 10 | 25.7 |
| 26 | 30 | 15.1 |
| 30 | 30 | 22.1 |
| 31 | 30 | 19.0 |
| 35 | 30 | 28.8 |
| 40 | 30 | 53.4 |
| 42 | 10 | 29.6 |
| 47 | 10 | 25.6 |
| 48 | 30 | 65.4 |
| 50 | 30 | 21.9 |
| 52 | 30 | 10.5 |
| 57 | 3 | 44.0 |
| 58 | 3 | 43.4 |
| 59 | 3 | 18.4 |
| 63 | 3 | 18.4 |
| 67 | 3 | 33.1 |
| 68 | 3 | 21.2 |
| 70 | 30 | 51.0 |
| Troglitazone | 300 | 34.0 |

EXAMPLE

The following Examples are provided only for the purpose of the preparation of the compound and not restrict the disclosed invention.

Example 1

4-[2-(5-Methyl-2-phenyl-1,3-oxazoleyl)ethoxy] benzene methylsulfonamide (a) 5-Methyl4-tosyloxyethyl-2-phenyl-oxazole 22.2 g of 5-Methyl-4-hydroxyethyl-2-phenyl-oxazole was dissolved in a mixture of pyridine (13 mL) and dichloroethane (6 mL) and toluenesulfonyl chloride was added slowly to the mixture and stirred at room temperature over night. The reaction mixture was poured into water and extracted with ethyl acetate (50 mL). The organic extract was washed with satd. $CuSO_4$ solution, $H_2O$ and satd. NaCl solution. Removal of solvents after drying over anhydro. $Na_2SO_4$, followed by column chromatography (ethyl acetate:n-hexane=1:1) yielded 3.33 g (87.6%) of a white solid of the objective compound.

MASS(m/e): 371 (M+),216,186(BP),156,130,105,77,51

IR($cm^{-1}$): 1359,1173,966,927,834,813,753,666

$^1$HNMR(CDCl$_3$) δ: 2.01–2.08 (m, 2H, —CH$_2$—), 2.29 (S, 3H, —CH$_3$), 2.42 (S, 3H, —CH$_3$), 2.55 (t, 2H, —CH$_2$—, J=6.83,7.33 Hz), 4.08 (t, 2H, —CH$_2$—, J=5.86,6.34 Hz), 7.31 (d, 2H, aromatic, J=7.81 Hz), 7.40–7.43 (m, 3H, aromatic), 7.78 (d, 2H, aromatic, J=8.3 Hz), 7.93 (dd, 2H, aromatic, J=7.33, 7.81 Hz)

(b) 5-Methyl-4-p-nitrophenoxyethyl-2-phenyl-1,3-oxazole 0.21 g of NaH was placed in a 50 mL flask and washed twice with n-hexane and added 10 mL of dimethylformamide. 0.67 g of p-nitrophenol was added to the solution at 0° C. and stirred for 30 min. To this mixture, the compound (1.8 g) obtained from the above mentioned step (a) in dimethyl formamide (5 mL) was added and stirred at 80° C. over night. After cooling, the reaction mixture was poured into water and the product was extracted with ethyl acetate (80 mL). The ethyl acetate phase was washed with $H_2O$, satd. NaCl solution and dried over $Na_2SO_4$ and filtered. Evaporation of the filtrate gave a residue, from which 1.24 g (75.6%) of the yellowish objective compound was obtained by silicagel column chromatography (ethyl acetate:n-hexane=1:3). m.p.=100–103° C.

MASS(m/e): 338(M+),200,173(BP),130,104,77,51

IR($cm^{-1}$): 1590,1500,1332,1263,1107,840

$^1$HNMR(CDCl$_3$) δ: 2.18–2.24 (m, 2H, —CH$_2$—), 2.29 (S, 3H, —CH$_3$), 2.71 (t, 2H, —CH$_2$—, J=7.33, 6.83 Hz), 4.09 (t, 2H, —CH$_2$—, J=6.35, 5.86 Hz), 6.95 (d, 2H, aromatic, J=9.28 Hz), 7.41–7.44 (m, 3H, aromatic), 7.97 (dd, 2H, aromatic, J=7.32, 7.82 Hz), 8.19 (d, 2H, aromatic, J=9.28 Hz)

(c) 5-Methyl-4-p-aminophenoxyethyl-2-phenyl-1,3-oxazole 1.23 g of the compound obtained from the above mentioned step (b) was dissolved in a solution of 25 mL of methanol-tetrahydrofuran (1:1) and added 0.25 g of 5% Pd—C. To this solution was introduced hydrogen-gas for 1 hour. After filtration of the reaction mixture, the filtrate was evaporated to give a residue, from which 1.02 g (91.1%) of the objective compound was obtained by silicagel column chromatography (ethyl acetate:n-hexane=1:1). m.p.=57–59° C.

MASS(m/e): 308(M+),200(BP),174,104,80,53

IR($cm^{-1}$): 1512,1242,825,711,681 $^1$HNMR(CDCl$_3$) δ: 2.08–2.15 (m, 2H, —CH$_2$—), 2.28 (S, 3H, —CH$_3$), 2.68 (t, 2H, —CH$_2$—, J=7.33, 7.32 Hz), 3.42 (bs, 2H, —NH$_2$), 3.90 (t, 2H, —CH$_2$—, J=6.35, 5.86 Hz), 6.62–6.66 (m, 2H, aromatic), 6.73–6.76 (m, 2H, aromatic), 7.38–7.45 (m, 2H, aromatic), 7.96–7.99 (m, 2H, aromatic)

(d) 4-[2-(5-Methyl-2-phenyl-1,3-oxazole-4-yl)ethoxy] benzene methylsulfonamide (compound 1)

To a mixture of 0.4 g of the compound obtained from the above mentioned step (c) and 0.28 mL of triethylamine in dichloroethane (4 mL) and 0.16 mL of mesyl chloride were added and stirred at 30° C. for 30 minutes. The reaction mixture was poured into water and extracted with ethyl acetate. The ethyl acetate phase was washed with satd. NH$_4$Cl solution, water and satd. NaCl solution and dried over anhydrous Na$_2$SO$_4$ and filtrated. Evaporation of the filtrate gave a residue, from which 0.34 g (66.7%) of the off-white objective compound was obtained by silicagel column chromatography (ethyl acetate:n-hexane=1:1). m.p.=121–123° C.

MASS(m/e): 372(M+),264,186(BP),149,104,79,55

IR(cm$^{-1}$): 3238,1506,1320,1281,1245,1212,1143,777

$^1$HNMR(CDCl$_3$) δ: 2.38 (S, 3H, —CH$_3$), 2.93 (S, 3H, —SO$_2$CH$_3$), 2.98 (t, 2H, —CH$_2$—, J=6.35, 6.84 Hz), 4.23 (t, 2H, —CH$_2$—, J=6.83, 6.84 Hz), 6.25 (S, 1H, —NH), 6.88 (d, 2H, aromatic, J=8.79 Hz), 7.16 (d, 2H, aromatic, J=9.27 Hz), 7.39–7.45 (m, 3H, aromatic), 7.97 (dd, 2H, aromatic, J=1.46, 1.95 Hz)

Example 2

4-[2-(5-Methyl-2-phenyl-1,3-oxazole-4-yl)ethoxy] benzene trifluoromethyl sulfonamide (compound 2)

To a mixture of the compound (0.4 g) obtained from Example 1 step (c) in 4 mL of dichloromethane and 0.27 mL of triethylamine was added trifluoromethanesulfonic acid anhydride (3.3 mL) and stirred for 30 minutes at 0° C. To the reaction mixture were added $_2$ mL of methanol and 1 mL of 10% NaOH solution and the mixture was stirred for 10 minutes, followed by addition of water (20 mL) and extracted with ethyl acetate. The extract was washed with satd. NH$_4$Cl, water and satd. NaCl and dried over anhydrous Na$_2$SO$_4$. After filtrating, the extract was evaporated and the residue was purified by silicagel column chromatography. Using a eluants (ethyletate:n-hexane=1:1), 0.38 g (66.7%) of the objective compound was obtained. m.p.=97–99° C.

MASS(m/e): 441(M+),200(BP),173,104,69

IR(cm$^{-1}$): 1455,1248,1215,1116,894,597

$^1$HNMR(CDCl$_3$) δ: 2.17–2.23 (m, 2H, —CH$_2$—), 2.29 (S, 3H, —CH$_3$), 2.70 (t, 2H, —CH$_2$—, J=6.83, 7.33 Hz), 4.05 (t, 2H, —CH$_2$—, J=5.86, 6.34 Hz), 6.97 (d, 2H, aromatic, J=8.79 Hz), 7.40–7.44 (m, 3H, aromatic), 7.98 (dd, 2H, aromatic, J=7.32, 8.30 Hz)

Example 3

5-Methyl-4-[2-(4-carboxymethylsulfonylamino) phenoxy]ethyl-2-phenyl-1,3-oxazole (compound 3)

(a) 5-Methyl-4-[2-(4-ethoxycarbonylmethyl sulfonylamino) phenoxy]ethyl-2-phenyl-oxazole To a solution of the compound (0.36 g) obtained from the above mentioned Example 1 step (c) and triethylamine (0.26 mL) in dichloroethane (8 mL) was slowly added ethoxy carbonyl chloride (0.27 g) at 0° C. and stirred for 2 hours. The reaction mixture was poured into water and the product was extracted with ethyl acetate. The extract was washed with satd. NH$_4$Cl, water and satd. NaCl and dried over anhydrous Na$_2$SO$_4$ and filtrated. Evaporation of the filtrate gave a residue, from which 0.32 g (59.1%) of the oily objective compound was obtained by silicagel column chromatography (ethyl acetate:n-hexane=1:1).

MASS(m/e): 443(M+),186(BP),144,108,84,47

IR(cm$^{-1}$): 1734,1341,1299,1248,1158,753

$^1$HNMR(CDCl$_3$) δ: 1.32 (t, 3H, —COOEt, J=6.84, 7.32 Hz), 2.38 (S, 3H, —CH$_3$), 2.98 (t, 2H, CH$_2$—, J=6.83, 6.35 Hz), 3.86 (S, 2H, —CH$_2$—), 4.23 (t, 2H, —CH$_2$—, J=6.83, 6.35 Hz), 4.28 (q, 2H, COOEt, J=7.32, 6.83 Hz), 6.74 (S, 1H, 13 SO$_2$NH), 6.88 (d, 2H, aromatic, J=8.78 Hz), 7.25 (d, 2H, aromatic, J=8.30 Hz), 7.39–7.44 (m, 3H, aromatic), 7.97 (q, 2H, aromatic, J=1.46, 1.96 Hz)

(b) 5-Methyl-4-[2-(4-carboxymethyl sulfonylamino) phenoxy]ethyl-2-phenyl-1,3-oxazole (compound 3)

To a solution of the compound (0.3 g) obtained from the above mentioned step (a) in ethanol (5 mL) was added 10% NaOH (2.5 mL) and the solution was stirred for 1 hour. After removing the solvent, the residue was dissolved in water and washed with ether. After acidification with 10% HCl,the water phase was extracted with ethyl acetate. The ethyl acetate phase was washed with water, satd. NaCl and dried over anhydrous Na$_2$SO$_4$. After removing the solvent, the residue was recruptized from ethyl acetate. 0.2 g (71.4%) of the objective compound was obtained. m.p.=164–167° C.

MASS(m/e): 371(M+—COOH),294,186(BP),144,104,77

IR(cm$^{-1}$): 3274,1713,1512,1338,1281,1245,1158,1107

$^1$HNMR (CDCl$_3$) δ: 2.42 (S, 3H, —CH$_3$), 3.06 (t, 2H, —CH$_2$—, J=6.35 Hz), 3.86 (S, 2H, —CH$_2$—), 4.24 (t, 2H, —CH$_2$—, J=6.83, 6.35 Hz), 6.85 (d, 2H, aromatic, J=9.28 Hz), 7.22 (d, 2H, aromatic, J=8.78 Hz), 7.45–7.47 (m, 3H, aromatic), 7.95 (q, $_2$H, aromatic, J=2.44, 3.9 Hz)

Example 4–5

According to the method described in Example 3, compound 4 (oil), compound 5 (m.p.=273–239° C.), compound 6 (m.p.=143–145° C.) and compound 7 (m.p.=114–116° C.) were obtained.

Example 8

2-[4-(2-(5-Methyl-2-phenyl-1,3-oxazole-4-yl) ethoxy)phenyl]amino-2-oxo-acetic acid (compound 8)

(a) 2-[4-(2-(5-Methyl-2-phenyl-1,3-oxazole-4-yl)ethoxy) phenyl]amino-2-oxo-acetic acid methyl aster A mixture of the compound (0.5 g) obtained from the above mentioned Example 1 step (c) and methyl oxalate (0.6 g) in methanol (10 mL) was refluxed over night. After cooling, the solvent was evaporated and a resulting residue was purified by silicagel column chromatography. Chloroform was used as a eluant. 0.55 g (84.6%) of the objective compound was obtained. m.p.=128–132

MASS(m/e): 380(M+),321,186(BP),144,105,59

$^1$HNMR(CDCl$_3$) δ: 2.37 (S, 3H, —CH$_3$), 2.98 (t, 2H, —CH$_2$—, J=6.84, 6.35 Hz), 3.96 (S, 3H, —COOMe), 4.24 (t, 2H, —CH$_2$—, J=6.35, 6.83 Hz), 6.90 (d, 2H, aromatic, J=8.79 Hz), 7.38–7.44 (m, 3H, aromatic), 7.53 (d, 2H, aromatic, J=8.79 Hz), 7.97 (d, 2H, aromatic, J=5.86 Hz), 8.76 (d, S, 1H, —NH)

(b) 2-[4-(2-(5-Methyl-2-phenyl-1,3-oxazole-4-yl)ethoxy) phenyl]amino-2-oxo-acetic acid (compound 8)

A mixture of the compound (0.53 g) obtained from the above mentioned Example 8 step (a) and 10% NaOH in methanol (15 mL) was stirred for 1 hour and water (30 mL) was added to the mixture, followed by acidification (pH 4) with 10% HCl to give a crptalline product. Recrystallization from ethyl acetate gave the objective compound (0.42 g, 82.3%). m.p.=196–198° C.

MASS(m/e): 366(M+),322,294,186(BP),144,104,77

$^1$HNMR(CDCl$_3$) δ: 2.36 (S, 3H, —CH$_3$), 2.92 (t, 2H, —CH$_2$—, J=6.35, 6.83 Hz), 3.32 (bs, 1H, —NH), 4.19 (t, 2H, —CH$_2$—, J=6.34, 6.84 Hz), 6.93 (d, 2H, aromatic, J=9.27 Hz), 7.45–7.55 (m, 3H, aromatic), 7.67 (dd, 2H, aromatic, J=2.44 Hz), 7.91 (dd, 2H, aromatic, J=1.47, 1.95 Hz)

Example 9

2-[4-(2-(5-Methyl-2-phenyl-1,3-oxazole-4-yl)ethoxy)benzyl]trifluoromethylsulfonamide (compound 9)

(a) 5-Methyl-4-(2-p-benzylaminophenoxy)-ethyl-2-phenyl-1,3-oxazole

A mixture of 5-methyl-4-[2-(p-formylphenoxy)]ethyl-2-phenyl-1,3-oxazole (0.54 g) and benzylamine (0.21 mL) in methanol (10 mL) was stirred for 10 minutes and $NaBH_3CN$ (0.11 g) was added to the mixture. The mixture was stirred over night and evaporated and to a resulting residue was added 10% HCl with stirring, followed by addition of satd. $NaHCO_3$ to alkalize. The product was extracted with ethyl acetate. The ethyl acetate phase was washed with $H_2O$, satd. NaCl and dried over anhydrous $Na_2SO_4$ and filtered. Evaporation of the filtrate gave a residue, from which 0.43 (61.4%) of the oily objective product was obtained by silicagel column chromatography.

MASS(m/e): 398(M+),291,212,186(BP),146,104,77

IR($cm^{-1}$): 3022,2914,1608,1509,1452,1242,738,714

$^1$HNMR($CDCl_3$) δ: 2.37 (S, 3H, —$CH_3$), 2.98 (t, 2H, —$CH_2$—, J=6.83, 6.84 Hz), 3.73 (S, 2H, —$CH_2$—), 3.78 (S, 2H, —$CH_2$—), 4.24 (t, 2H, —$CH_2$—, J=6.84, 6.83 Hz), 6.86 (d, 2H, aromatic, J=8.79 Hz), 7.21–7.44 (m, 10H, aromatic), 7.97 (q, 2H, aromatic, J=1.46, 1.95 Hz)

(b) 5-Methyl-4-(2-p-aminophenoxy)ethyl-2-phenyl-1,3-oxazole

The compound (0.4 g) obtained from the above mentioned Example 9 step (a) was dissolved in methanol (10 mL) containing a small amount of HOAc and 5% Pd-C (80 mg). The mixture is hydrogenated and the reaction mixture was filtered and the filtrate was evaporated. A resulting residue was purified by silicagel column chromatography using a eluant ($CHCl_3$:MeOH=10:1). The objective compound (0.21 g, 67.7%) was obtained. m.p.=149–152° C.

MASS(m/e): 308(M+),291,186(BP),144,122,104,77

IR($cm^{-1}$): 3430,2962,1608,1248

$^1$HNMR($CDCl_3$) δ: 3.88 (S, 2H, —$CH_2$—), 4.23 (t, 2H, —$CH_2$—, J=6.34, 6.84 Hz), 6.90 (d, 2H, aromatic, J=8.79 Hz), 7.27 (d, 2H, aromatic, J=8.78 Hz), 7.41–7.46 (m, 3H, aromatic), 7.96 (d, 2H, aromatic, J=7.81 Hz)

(c) 2-[4-(2-(5-Methyl-2-phenyl-1,3-oxazole-4-yl)ethoxy)benzyl]trifluoromethyl sulfonamide (compound 9)

The compound (0.14 g) obtained from the above mentioned Example 9 step (b) was reacted with trifluoromethanesulfonamide as same manner as Example 2 and the objective compound (compound 9) was obtained (0.55 g, 28%). m.p.=113–115° C.

MASS(m/e): 440(M+),186,144,104(BP),77

IR($cm^{-1}$): 3310,1443,1368,1251,1227,1188,1146

$^1$HNMR($CDCl_3$) δ: 2.38 (S, 3H, —$CH_3$), 2.98 (t, 2H, —$CH_2$—, J=6.83, 6.84 Hz, 4.25 (t, 2H, —$CH_2$—, J=6.84, 6.34 Hz), 4.37 (d, 2H, —$CH_2$—, J=4.89 Hz), 5.05 (bs, 1H, —$NHSO_2$—), 6.90 (d, 2H, aromatic, J=8.79 Hz), 7.22 (d, 2H, aromatic, J=8.79 Hz), 7.41–7.45 (m, 3H, aromatic), 7.97 (q, 2H, aromatic, J=1.95, 1.96 Hz)

Example 10

4-[2-(5-Ethylpyridine-2-yl)ethoxy]benzene trifluoromethylsulfonamide (compound 10)

(a) 2-[2-(4-Nitrophenoxy)]ethyl-5-ethyl-pyridine

To a mixture of 2-(5-ethylpyridine) ethanol (10 g) and 4-fluoronitrobenzene (9.3 g) in Dimethylformamide (100 mL) was added NaOH (3.4 g) and the mixture was stirred at 0° C. for 1 hour. After pouring into ice-water, the product was extracted with ethyl acetate (150 mL). The ethyl acetate phase was washed with satd. NaCl and dried over anhydrous $Na_2SO_4$. After removing the solvent, the resulting residue was purified by silicagel column chromatography (EtoAc:n-hexane=1:2→2:1). Recrystallization from EtOAc n-hexane mixture (1:1) gave the off-white objective compound. 13.4 g (74.4%), m.p.=45–47° C.

MASS(m/e): 272(M+),150,134(BP),119,93,77

IR($cm^{-1}$): 1593,1518,1491,1341,1260,1008,834

$^1$HNMR($CDCl_3$) δ: 1.25 (t, 3H, —$C_2H_5$, J=7.81, 7.32 Hz), 2.64 (q, 2H, —$C_2H_5$, J=7.33, 7.32 Hz), 3.27 (t, 2H, —$CH_2$—, J=6.34, 6.84 Hz), 4.46 (t, 2H, —$CH_2$—, J=6.34, 6.84 Hz) 7.17 (d, 1H, pyridine, J=8.31 Hz), 7.47 (dd, 1H, pyridine, J=2.44, 2.45 Hz), 8.18 (dd, 2H, aromatic, J=6.83, 7.32 Hz), 8.40 (d, 1H, pyridine, J=1.95 Hz)

(b) 2-[2-(4-Aminophenoxy)]ethyl-5-ethyl-pyridine

The compound (1.85 g) obtained from the above mentioned Example 10 step (a) was hydrogenated as same manner as Example 1 step (c) and obtained the oily objective compound (1.62 g, 98.2%).

MASS(m/e): 242(M+),134(BP),119,106,83,65

IR($cm^{-1}$): 2950,1509,1233,822

$^1$HNMR($CDCl_3$) δ: 1.24 (t, 3H, 13 $C_2H_5$, J=7.81, 7.33 Hz), 2.62 (q, 2H, —$C_2H_5$, J=7.33 Hz), 3.19 (t, 2H, —$CH_2$—, J=6.35, 6.83 Hz), 3.42 (bs, 2H, —$NH_2$), 4.26 (t, 2H, —$CH_2$—, J=6.35, 6.84 Hz), 6.61–6.64 (m, 2H, aromatic), 6.72–6.76 (m, 2H, aromatic), 7.18 (d, 1H, pyridine, J=7.81 Hz), 7.44 (dd, 1H, pyridine, J=1.95, 1.96 Hz), 8.39 (d, 1H, pyridine, J=2.46 Hz)

(c) 4-[2-(5-Ethylpyridine-2-yl)ethoxy]benzene trifluoromethylsulfonamide (compound 10)

The compound (1.2 g) obtained from the above mentioned Example 10 step (b) was reacted with tuoromethanesulfonic acid anhydride by the same procedure described in Example 2 and obtained 0.3 g the objective compound (compound 10). m.p.=76–78° C.

MASS(m/e): 373(M+–1),134(BP),91,69

IR($cm^{-1}$): 1446,1263,1119,897,603

$^1$HNMR($CDCl_3$) δ: 1.25(t, 3H, 13 $C_2H_5$, J=7.81, 7.33 Hz), 2.63 (q, 2H, —$C_2H_5$, J=7.32, 7.82 Hz), 3.25 (t, 2H, —$CH_2$—, J=6.83, 6.35 Hz), 4.39 (t, 2H, —$CH_2$—, J=6.35 Hz), 6.96 (dd, 2H, aromatic, J=6.84, 6.83 Hz), 7.18 (d, 1H, pyridine, J=7.81 Hz), 7.28 (d, 2H, aromatic, J=9.28 Hz), 7.46 (dd, 1H, pyridine, J=7.81 Hz), 8.40 (d, 1H, pyridine, J=1.96 Hz)

Example 11

4-[2-(N-Methyl-N-2-pyridyl)aminoethoxy]benzene trifluoromethanesulonamide (compound 11)

(a) 4-[2-(N-Methyl-N-2-pyridyl)aminoethoxy]-1-nitrobenzene-2-pyridyl-2-methylamino ethanol (4.0 g) was reacted with 4-fluorobenzene by the same procedure described in Example 6 step (a) and obtained the oily objective compound (5.9 g, 82.2%).

MASS(m/e): 273(M+),139,121 (BP),94,78,51

IR($cm^{-1}$): 2926,1590,1497,1425,1338,1260

$^1$HNMR($CDCl_3$) δ: 3.14 (S, 3H, —$CH_3$), 4.03 (t, 2H, —$CH_2$, J=5.86, 5.37 Hz) 4.30 (t, 2H, —$CH_2$—, J=5.86 Hz), 5.52 (d, 1H, pyridine, J=8.79 Hz), 6.59 (t, 1H, pyridine, J=4.88, 6.35 Hz), 6.97 (dd, 2H, aromatic, J=8.79 Hz), 7.45–7.50 (m, 1H, pyridine), 8.15–8.20 (m, 2H, pyridine, aromatic)

(b) 4-[2-N-Methyl-N-2-pyridyl)aminoethoxy]-1-aminobenzene

The compound (5.85 g) obtained from the above mentioned Example 11 step (a) was hydrogenated by the same procedure described in Example 1 step (c) and obtained the objective compound (2.12 g, 40.7%).

MASS(m/e): 243(M+),135(BP),121,108,94,78,65

IR(cm$_{-1}$): 3334,2914,1596,1557,1503,1425,1233,771

(c) 4-[2-(N-Methyl-N-2-pyridyl)aminoethoxy]benzene trifluoromethanesulfonamide (compound 11)

The compound (0.5 g) obtained from the above mentioned Example 11 step (b) was reacted with trifluoromethanesulfonamide by the same procedure described in Example 2 and obtained the objective product (0.67 g, 87.0%). m.p.=60–62° C.

MASS(m/e): 375(M+),304,170,135,108,78(BP),52

IR(cm$^{-1}$): 1593,1503,1452,1218,1125,891,600

$^1$HNMR(CDCl$_3$) δ: 3.13 (S, 3H, —CH$_3$), 4.01 (t, 2H, —CH$_2$, J=5.86, 5.37 Hz), 4.24 (t, 2H, —CH$_2$—, J=5.86, 5.37 Hz), 6.51 (d, 1H, pyridine, J=8.30 Hz), 6.57 (t, 1H, pyridine, J=4.88, 6.84 Hz), 6.97 (d, 2H, aromatic, J=9.27 Hz), 7.27 (d, 2H, aromatic, J=9.77 Hz), 7.44–7.49 (m, 1H, pyridine), 8.15 (d, 1H, pyridine, J=3.90 Hz)

Example 12–17

According to the method described in Example 1, compound 12 (m.p.=106–108° C.), compound 13(m.p.=67–68° C.), compound 14 (m.p.=56–58° C.), compound 15 (m.p.=128–130° C.), compound 16 (126–127° C.) and compound 17 (m.p.=128–130° C.) were obtained.

Example 18–20

According to the method described in Example 2, compound 18 (m.p.=197–198° C.), compound 19 (m.p.=70–71° C.) and compound 20 (m.p.=170–172° C.) were obtained.

Example 21

5-Methyl-4-(3-hydroxy)propyl-2-phenyl-1,3-oxazole, prepared from glutamic acid instead of asparatic acid, was reacted as a similar manner described in Experimental 2 and obtained compound 21 (m.p.=113–114° C.).

Example 22–24

According to the same procedure described in Example 4, compound 22 (m.p.=128–130° C.) and compound 23 (m.p.=217° C. (decomp.)) were obtained.

Example 25

2-Hydroxy-4-[2-(5-methyl-2-phenyl-1,3-oxazole-4-yl)ethoxy]benzoic acid methyl ester (compound 25)

0.2 g of methyl 2-4-dihydroxybenzoate and 0.23 g of diisopropyl azodicarboxylate (DIAD) were dissolved in 2 mL of THF. To this mixture was slowly added a mixture of 0.29 g of 5-methyl-4-hydroxyethyl-3-phenyl-1,3-oxazole and 0.31 g of Ph$_3$P in 3 mL of THF and the mixture was subjected to Mitsunobu reaction. After the reaction mixture was allowed to stand over night, the solvent was removed. The resulting residue was purified by silicagel column chromatography (ethyl acetate:benzene=1:5). After removing the solvent, the residue was recrystallized from benzene. 0.31 g (73.3%) of the colorless objective compound was obtained. m.p.=133–134° C.

MASS(m/e): 353(M+),217,185,136,104(BP),77,53

IR(cm$^{-1}$): 1677,1617,1440,1320,1251,1188,1134

$^1$HNMR(CDCl$_3$) δ: 3.90 (S, 3H, —COOMe), 4.27 (t, 2H, —CH$_2$, J=6.34, 6.84 Hz), 6.42 (dd, 1H, aromatic, J=8.79 Hz), 6.46 (d, 1H, aromatic, J=2.44 Hz), 7.39–7.44 (m, 3H, aromatic), 7.72 (d, 1H, aromatic, J=9.28 Hz), 7.97 (q, 2H, aromatic, J=7.33, 8.3 Hz), 10.93 (s, 1H, —OH)

Example 26–28

According to the procedure described in Example 11, compound 26 (m.p.=211–213° C.), compound 27 (m.p.=85–87° C.) compound 28 (m.p.=130–132° C.) were obtained.

Example 29–30

2-Hydroxy-4-[2-(5-methyl-2-phenyl-1,3-oxazole-4-yl)ethoxy]benzoic acid (compound 29)

0.17 g of the compound obtained from Example 20 was dissolved in 2 mL of MEOH: THF (1:1).

To the solution was added 2 mL of 10% NaOH and the mixture was refluxed for 1 hour. After removal of the solvent, the residue was washed with ether, followed by acidification with 10% HCl. The resulting precipitate was filtered. Recrystallization from ethanol gave the colorless objective compound (0.13 g, 81.3%). m.p.=192–194° C.

MASS(m/e): 339(M+),295,217,186,104(BP)

IR(cm$^{-1}$): 2920,1655,1260,1170

According to the above mentioned procedure compound 30 was obtained. (m.p.=246–266° C.).

Example 31–32

2-Ethoxy4-[2-(5-methyl-2-phenyl-1,3-oxazole-4-yl)ethoxy]benzoic acid (compound 31)

(a) 2-Ethoxy-4-[2-(5-methyl-2-phenyl-1,3-oxazole-4-yl)ethoxy]benzoic acid methyl ester To a solution of the compound 25 (0.27 g) in DMF (5 mL) was added K$_2$CO$_3$ (0.16 g) and EtI (0.07 mL) and the mixture was allowed to stand over night. The reaction mixture was poured into water and the product was extracted with ethyl acetate (30 mL). The ethyl acetate phase was washed with water, satd. NaCl and dried over anhydrous Na$_2$SO$_4$ and filtrated. Evaporation of the filtered gave a residue, from which 0.28 g (96.6%) of the colorless objective compound was obtained by silicagel column chromatography (ethyl acetate:n-hexane=1:3).

MASS(m/e): 381(M+),217,186,144,104(BP),77,51

IR(cm$^{-1}$): 2926,1686,1605,1257,1194

(b) 2-Ethoxy-4-[2-(5-methyl-2-phenyl-1,3-oxazole-4-yl)ethoxy]benzoic acid (compound 31)

The compound obtained from above mentioned Example 31–32 step (a) was hydrolyzed by the procedure in Example 29 and obtained the objective compound (0.22 g). m.p.=128–130° C.

MASS(m/e): 367(M+),217,186,144,104(BP),77,51

IR(cm$^{-1}$): 1686,1605,1572,1281,1263,1239,1191

$^1$HNMR(CDCl$_3$) δ: 2.99 (t, 2H, —CH$_2$—, J=6.84 Hz), 4.25 (q, 2H, oEt, J=6.84 Hz), 4.33 (t, 2H, —CH$_2$—, J=6.34, 6.84 Hz), 6.50 (d, 1H, aromatic, J=2.44 Hz), 6.55 (dd, 1H, aromatic, J=1.95 Hz), 7.41–7.44 (m, 3H, aromatic), 7.96–7.99 (m, 2H, aromatic), 8.10 (d, 1H, aromatic, J=8.79 Hz)

And compound 25 was reacted with methoxy methylchloride to obtain compound 32. m.p.=129–130° C.

Example 33–38

Each compounds of 3-benzyl-4-nitrophenol-2,6-difluoro-4-nitrophenol and 5-methyl-4-hydroxyethyl-2-phenyl-1,3- oxazole were subjected to Mitsunobu reaction in a similar manner described in Example 25 and the nitro compounds were obtained, followed by the procedures described in Example 1 step (c) and step (d) yielded compound 33 (m.p.=155–156° C.), compound 35 (m.p.=143–144° C.) and compound 36 (m.p.=78–80° C.). Further, Mitsunobu reaction of 2,4-dihydroxy-benzene sulfonamide and 5-methyl-4-hydroxy-3-phenyl-1,3-oxazole yielded compound 34 (m.p.=231–232° C.). Ethylation of the compound 34 yielded compound 37 (m.p.=171–173° C.). Methyl-4-hydroxy-2-ethoxyphenoxy acetate was reacted in a similar manner and the resulting compound was hydrolyzed to obtain compound 38 (m.p.=154–156° C.).

Example 39

4-[2-(N-Methyl-N-2-pyridyl)aminoethoxy]-2-hydroxyphenyl trifluoromethane sulfonamide (compound 39)

(a) 4-[2-(N-Methyl-2-N-pyridyl)aminoethoxy]-2-hydroxy nitrobenzene

To a mixture of 2-(N-methyl, N-hydroxyethyl)-aminopyridine (0.35 g) and 4-fluoro-2-methoxy-methyloxy-nitrobenzene in DMF (30 mL) was added NaH (0.12 g) and stirred at room temperature over night. The reaction mixture was poured into ice-water and extracted with ethyl acetate. The ethyl acetate extract was washed with satd. NHCl and dried over anhyd. $Na_2SO_4$ and filtered. After removal of solvent, the residue was purified by silicagel column chromatography (ethyl acetate:n-hexane=1:2). The oily objective compound (0.44 g, 57.1%) was obtained.

MASS(m/e): 333(M+),121(BP),78,52
IR($cm^{-1}$): 2926,1596,1500,1425,1341,1287,1152

(b) 4-[2-(N-Methyl-N-2-pyridyl)aminoethoxy]-2-hydroxyphenyl trifluoromethanesulfonamide (compound 33)

The compound obtained from the above mentioned step (a) was reduced with hydrogen in a similar manner described in Example 1 step (c) and the resulting compound was reacted with trifluoromethanesulfonic acid anhydride in a similar manner described in Experimental 1 step (d). After removing of the protection group (MOM, methoxymethyl), the residue was recrystallize from the mixture of ethyl acetate and n-hexane to obtain the colorless objective compound (compound 33). mp–134–135° C.

MASS(m/e): 391 (M+),135(BP),107,78
IR($cm^{-1}$): 1611,1509,1419,1404,1227,1176,1146
$^1$HNMR($CDCl_3$) δ: 3.14 (S, 3H, Me), 3.93 (t, 2H, —$CH_2$, J=5.37 Hz), 4.11 (2H, —$CH_2$—, J=5.37 Hz), 6.37–6.43, 6.53–6.59 (m, m, 4H, aromatic, pyridine), 7.27 (d, 1H, aromatic, J=8.79 Hz), 7.46–7.51 (m, 1H, pyridine), 8.08 (d, 1H, pyridine, J=4.88 Hz)

Example 40–41

Compound 40 (m.p.=133–135° C.) and compound 41(m.p.=151–153° C.) were obtain from 4-fluoro-2-ethoxy-nitrobenzene by proceeding in a similar manner described in Experimental 39 step (a).

Example 42–45

In stead of 2-(N-Methyl, N-hydroxyethyl) aminopyridine in Example 39 step (a), 5-methyl-4-hydroxy-2-phenyl-1,3-oxazole was reacted in a similar manner and the resulting compound was reacted with trifluoromethanesulfonic acid anhydride to obtain compound 43 (m.p.=169–171° C.). The compound obtained from Example 39 step (a) was reacted with trifluoromethanesulfonic acid anhydride to obtain compound 44 (m.p.=124–125° C.). Further, 2-(N-Methyl, N-hydroxyethyl)-amino pyridine in Example 39 step (a) was reacted with 4-fluoro-2-methoxy-nitrobenzene and the resulting product was treated with in a similar manner described in Example 1 step (c) to obtain the oily objective compound 45.

Example 46–47

N-Butyl-2,4-dihydroxy-benzenesulfonamide and 5-methyl$_4$-bromoethyl-2-phenyl-1,3-oxazole was reacted in a similar manner described in Example 1 step (b) to obtain compound 46 (m.p.=137–139° C.). After reacting 2,6-dibromo-4-hydroxy-benzoic acid methyl ester and 5-methyl-4-bromoetyl-2-phenyl-1,3-oxazole, compound 47 (m.p.=163–164° C.) was obtained.

Example 48–54

After chlorination of the compound of general formula (68), the resulting compound was reacted with 4-nitroaniline or corresponding aniline to obtain the compound of general formula (69), followed by reduction in a similar manner described in Example 1 and the resulting compounds were treated in a similar manner described in Example 2. The following objective compounds were obtained. Compound 53 was hydrolyzed to obtain compound 54. Compound 48 (m.p.=147–149° C.), compound 49 (m.p.=175–177° C.), compound 50 (m.p=166–168° C.), compound 51 (m.p.= 164–166° C.), compound 52 (m.p.=227–229° C.), compound 53 (oil), compound 54 (175° C., decomp.)

Example 55–56

After activation of carboxylic acid group in general formula (71) by the reported method (Bioorg.Med.Chem.Lett.,1995,1155), the resulting compound was reacted with sulfamines in the presence of DBU to obtain compound 55 (m.p.=150–152° C.) and compound 56 (m.p.=214–216° C.).

Example 57–59

Instead of 5-methyl-4-p-aminophenoxy-2-phenyl-1,3-oxazole in Example 2, 5-methyl-4-p-aminophenoxyethyl-2-p-tolyl-1,3-oxazole, 5-methyl-4-p-aminophenoxyethyl-2-p-chlorophenyl-1,3-oxazole and 5-methyl-4-p-aminophenoxyethyl-2-p-fluorophenyl-1,3-oxazole were reacted in a similar manner described in Example 2 to obtain the following compounds. Compound 57 (m.p.=173.5–175° C.), compound 58 (m.p.=189–190° C.), compound 59 (m.p.=161–163° C.).

Example 60–63

Instead of 5-methyl-4-p-aminophenoxy-2-phenyl-1,3-oxazole, 5-isopropyl-4-p-aminophenoxy-ethyl-2-p-tolyl-1,3-oxazole, 5-isopropyl-4-p-aminophenoxy-2-phenyl-1,3-oxazole, 5-isopropyl-4-p-aminophenoxyethyl-2-p-fluorophenyl-1,3-oxazole and 5-isopropyl$_4$-p-aminophenoxy-2-(3,5-di-t-butyl-4-hydroxy)phenyl-1,3-oxazole were reacted in a similar manner described in Example 2 to obtain the following compounds. Compound 60 (m.p.=190–191° C.), compound 61 (m.p.=155–156° C.), compound 62 (m.p.=189–190° C.), compound 63 (m.p.= 142–144° C.).

Example 64–66

5-Isopropyl-4-hydroxyethyl-2-phenyl-1,3-oxazole, 5-isopropyl-4-hydroxyethyl-2-p-phenyl-1,3-oxazole and 5-isopropyl-4-hydroxyethyl-2-p-tolyl-1,3-oxazole were reacted with 4-fluoro-2-ethoxy-nitrobenzene in a similar manner described in Example 39 to obtain the following compounds. Compound 64 (m.p.=142–144° C.), compound 65 (m.p.=179–181° C.), Compound 66 (m.p.=124° C.).

Example 67–68

Each of 5-methyl-4-hydroxyethyl-2-(p-ethoxycarbonylmethyloxy)phenyl-1,3-oxazole and 5-methyl-4-hydroxyethyl-2-(3,5-di-t-butyl-4-ethoxycarbonylmethyloxy)phenyl 1,3-oxazole were transformed to 5-methyl-4-p-nitrophenyl-2-(p-ethoxycarbonylmethyloxy)phenyl-1,3-oxazole and 5-methyl-4p-nitrophenyl-2-(3,5-di-t-butyl-4-ethoxycarbomethyloxy)phenyl-1,3-oxazole using a similar method described in Example 39. The resulting compounds were hydrolyzed with 10% NaOH—MeOH to obtain the following compounds. Compound 67 (m.p.=167–168° C.), compound 68 (m.p.=196–198° C.).

Example 69

5-Methyl-4-p-formylphenyl-2-phenyl-1,3-oxazole (1.0 g) was dissolved in dichlolomethane (10 mL) and hydroxylamine-o-sulfonic acid (0.59 g) was added. The mixture was stirred for 30 minutes and the resulting precipitate was collected, followed by washing with water, MeOH and dichloromethane. 1.03 g of compound 69 was obtained. m.p.=165–167°

MASS(m/e): 403(M+1),401(M−1)

Example 70

According to a similar procedure, described in Example 2, 5-methyl-4-aminophenoxyethyl-2-(3-t-butyl-4-hydroxy) phenyl-1,3-oxazole was transformed to compound 70. m.p.= 58–60° C.

EFFECTS OF THE INVENTION

This invention concerns to novel ether and/or amide derivatives which enhance insulin action and show hypoglycemic activities with low toxicities and useful for antidiabetics.

What is claimed is:

1. A compound of the formula (I), $$R_1 - A - R_2 \quad (I)$$

wherein

A is —O— or —NH—C(=O)—;

$R_1$ is 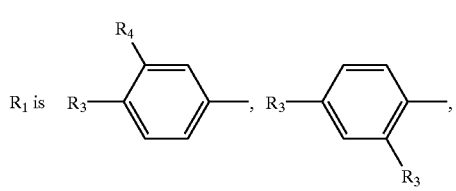,

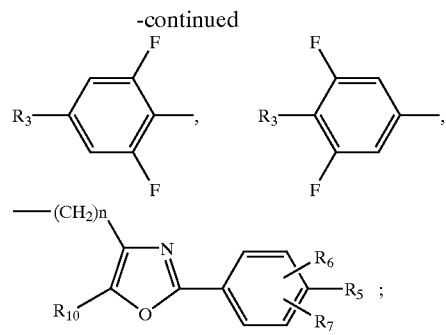

with the proviso that (i) when A is —O—, then n is 2 or 3, and (ii) when

A is —NH—C(=O)—, then n is 1 or 2;

$R_3$ is $CH_3SO_2NH$—, $CF_3SO_2NH$—, $CH_3SO_2NH$—, $CH_3SO_2NHCH_2$—, $CF_3SO_2NHCH_2$—,

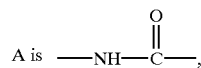

$HOOC$—$CH_2SO_2NH$—, $CF_3$—$CH_2SO_2NH$—,

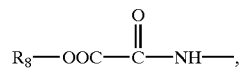

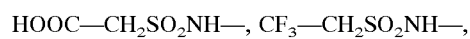

$R_8$ —$NHSO_2$—$CH_2$, $HOOC$—$CH_2$—$O$—, $HSO_3N$=$CH$—, or $R_9$—$SO_2NHCO$—;

$R_4$ is H, OH, O-alkyl or O—$CH_2OCH_3$;

$R_5$ is halogen atom, —$CH_2COOH$ or OH;

$R_6$ and $R_7$ are hydrogen, t-butyl or pyrolidyl;

$R_8$ is hydrogen or lower alkyl;

$R_9$ is alkyl;

$R_{10}$ is lower alkyl;

or a pharmaceutically acceptable salt thereof.

2. A compound of claim 1, wherein $R_1$ is 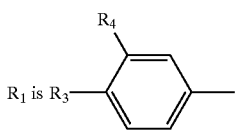

wherein $R_3$ and $R_4$ have the above-mentioned meanings, or a pharmaceutically acceptable salt thereof.

3. A compound of claim 1, wherein $R_2$ is 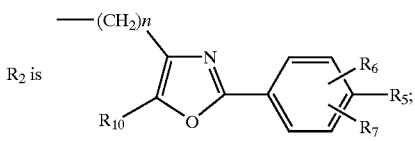

wherein, $R_5$ is H, halogenaton or OH; and $R_6$ and $R_7$ is H or t-butyl; $R_{10}$ is lower alkyl or a pharmaceutically acceptable salt thereof.

4. A pharmaceutical composition effective for use in the treatment of diabetes comprising a pharmacologically effective amount of a compound of general formula (I) according to claim 1.

5. A process for the production of a compound of general formula (I) according to claim 1, wherein, A is —O—;

$R_1$ is 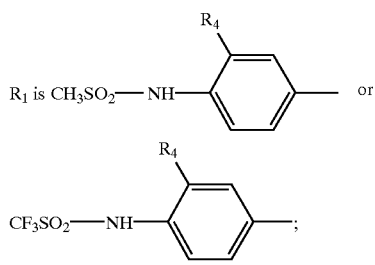 or $R_4$ has the above-mentioned meaning, which comprises reducing a compound (A) of general formula

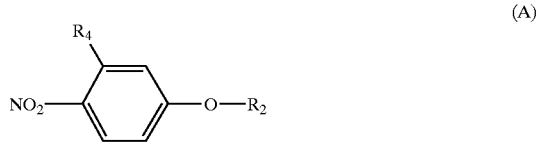 (A)

in which $R_2$ and $R_4$ have the above-mentioned meanings to obtain a compound (B) of general formula

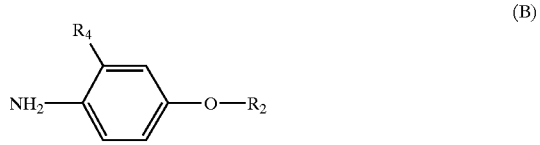 (B)

in which $R_2$ and $R_4$ have the above-mentioned meanings, and reacting compound (B) with $CH_3SO_2Cl$ or $CF_3SO_2Cl$ to obtain the compound of the general formula (I).

* * * * *